(12) United States Patent
Bosua

(10) Patent No.: US 11,832,926 B2
(45) Date of Patent: *Dec. 5, 2023

(54) NON-INVASIVE DETECTION OF AN ANALYTE AND NOTIFICATION OF RESULTS

(71) Applicant: Know Labs, Inc., Seattle, WA (US)

(72) Inventor: Phillip Bosua, Seattle, WA (US)

(73) Assignee: KNOW LABS, INC., Seattle, WA (US)

( * ) Notice: Subject to any disclaimer, the term of this patent is extended or adjusted under 35 U.S.C. 154(b) by 430 days.

This patent is subject to a terminal disclaimer.

(21) Appl. No.: 17/171,279

(22) Filed: Feb. 9, 2021

(65) Prior Publication Data

US 2021/0259571 A1 Aug. 26, 2021

Related U.S. Application Data

(60) Provisional application No. 62/979,149, filed on Feb. 20, 2020.

(51) Int. Cl.
*A61B 5/145* (2006.01)
*A61B 5/00* (2006.01)
(Continued)

(52) U.S. Cl.
CPC .......... *A61B 5/0507* (2013.01); *A61B 5/0004* (2013.01); *A61B 5/1455* (2013.01);
(Continued)

(58) Field of Classification Search
CPC ... A61B 5/0507; A61B 5/0004; A61B 5/1455; A61B 5/14532; A61B 5/7405; A61B 5/742; A61B 5/7455; A61B 5/145
See application file for complete search history.

(56) References Cited

U.S. PATENT DOCUMENTS 4,202,000 A 5/1980 Carballes
8,223,021 B2 7/2012 Goodnow et al.
(Continued)

FOREIGN PATENT DOCUMENTS

EP 3146898 B1 11/2018
EP 3981329 A1 4/2022
(Continued)

OTHER PUBLICATIONS

Hanna, J et al., "Noninvasive, wearable, and tunable electromagnetic multisensing system for continuous glucose monitoring, mimicking vasculature anatomy," Science Advances, 6, eaba5320, 2020 (11 pages).
(Continued)

*Primary Examiner* — Chu Chuan Liu
(74) *Attorney, Agent, or Firm* — Hamre, Schumann, Mueller & Larson, P.C.

(57) ABSTRACT

A method for providing notification regarding one or more analytes includes detecting an amount of each of the one or more analytes using a non-invasive sensor, determining a notification to present based on the amount of at least one of the one or more analytes and notification criteria using a processor, and sending an instruction directing presentation of the notification. The method can further include presenting the notification. The notification can include vibration, sound, or visible components such as light, text, or images. The notification criteria can include upper thresholds, lower thresholds, or the analyte being within or outside of bounded ranges. Systems performing the method can include the sensor and optionally one or more of a mobile device and a remote server, and the notification can be presented in a device including the sensor or a separate device such as the mobile device.

20 Claims, 10 Drawing Sheets

(51) Int. Cl.
*A61B 5/0507* (2021.01)
*A61B 5/1455* (2006.01)

(52) U.S. Cl.
CPC ........ *A61B 5/14532* (2013.01); *A61B 5/7282* (2013.01); *A61B 5/742* (2013.01); *A61B 5/7405* (2013.01); *A61B 5/7455* (2013.01)

(56) References Cited

U.S. PATENT DOCUMENTS

| | | | |
|---|---|---|---|
| 9,198,607 | B2 | 12/2015 | Fischer |
| 9,864,024 | B2 | 1/2018 | Vester |
| 10,149,629 | B2 | 12/2018 | Szczepaniak et al. |
| 10,478,101 | B1 | 11/2019 | Cespedes et al. |
| 10,548,503 | B2 | 2/2020 | Bosua |
| 10,617,296 | B2 | 4/2020 | Sloan et al. |
| 10,856,766 | B2 | 12/2020 | Leabman |
| 10,912,500 | B2 | 2/2021 | Poeze et al. |
| 10,956,950 | B2 | 3/2021 | Al-Ali et al. |
| 11,058,317 | B1 * | 7/2021 | Bosua ................ A61B 5/14532 |
| 11,202,582 | B2 | 12/2021 | Verkruijsse et al. |
| 11,244,753 | B2 | 2/2022 | Haggerty et al. |
| 11,291,374 | B2 | 4/2022 | Lee et al. |
| 11,298,037 | B2 | 4/2022 | Leabman |
| 11,350,830 | B2 | 6/2022 | McKenna et al. |
| 11,360,188 | B2 | 6/2022 | Leabman |
| 11,367,525 | B2 | 6/2022 | Addison et al. |
| 11,389,093 | B2 | 7/2022 | Triman et al. |
| 11,426,104 | B2 | 8/2022 | Schurman et al. |
| 2003/0036713 | A1 | 2/2003 | Bouton et al. |
| 2004/0065158 | A1 | 4/2004 | Schrepfer et al. |
| 2004/0127777 | A1 | 7/2004 | Ruchti et al. |
| 2004/0133086 | A1 | 7/2004 | Ciurczak et al. |
| 2009/0275814 | A1 | 11/2009 | Watanabe et al. |
| 2010/0041969 | A1 | 2/2010 | Beise |
| 2011/0028814 | A1 | 2/2011 | Petersen et al. |
| 2014/0213870 | A1 | 7/2014 | Hsu et al. |
| 2016/0051171 | A1 | 2/2016 | Pikov et al. |
| 2017/0095667 | A1 | 4/2017 | Yakovlev et al. |
| 2018/0028824 | A1 | 2/2018 | Pivonka et al. |
| 2019/0008422 | A1 | 1/2019 | Leath et al. |
| 2019/0053741 | A1 | 2/2019 | Chaudhry |
| 2019/0104939 | A1 | 4/2019 | Costantine et al. |
| 2019/0269853 | A1 | 9/2019 | Doyle et al. |
| 2019/0388000 | A1 | 12/2019 | Costantine et al. |
| 2020/0054255 | A1 | 2/2020 | Conrad et al. |
| 2020/0057163 | A1 | 2/2020 | Bromberg |
| 2020/0146584 | A1 | 5/2020 | Bosua |
| 2020/0187791 | A1 | 6/2020 | Leabman |
| 2020/0187792 | A1 | 6/2020 | Leabman |
| 2020/0187793 | A1 | 6/2020 | Leabman |
| 2020/0187812 | A1 | 6/2020 | Leabman |
| 2020/0187813 | A1 | 6/2020 | Leabman |
| 2020/0187814 | A1 | 6/2020 | Leabman |
| 2020/0187815 | A1 | 6/2020 | Leabman |
| 2020/0187816 | A1 | 6/2020 | Leabman |
| 2020/0187817 | A1 | 6/2020 | Leabman |
| 2020/0187818 | A1 | 6/2020 | Leabman |
| 2020/0187819 | A1 | 6/2020 | Leabman |
| 2020/0187820 | A1 | 6/2020 | Leabman |
| 2020/0187836 | A1 | 6/2020 | Leabman |
| 2020/0187837 | A1 | 6/2020 | Leabman |
| 2020/0187867 | A1 | 6/2020 | Leabman |
| 2020/0191909 | A1 | 6/2020 | Leabman |
| 2020/0191932 | A1 | 6/2020 | Leabman |
| 2020/0191933 | A1 | 6/2020 | Leabman |
| 2020/0191944 | A1 | 6/2020 | Leabman |
| 2020/0191945 | A1 | 6/2020 | Leabman |
| 2020/0191947 | A1 | 6/2020 | Leabman |
| 2020/0192426 | A1 | 6/2020 | Leabman |
| 2020/0192427 | A1 | 6/2020 | Leabman |
| 2020/0192428 | A1 | 6/2020 | Leabman |
| 2020/0193326 | A1 | 6/2020 | Leabman |
| 2020/0195197 | A1 | 6/2020 | Leabman |
| 2020/0195293 | A1 | 6/2020 | Leabman |
| 2022/0015695 | A1 | 1/2022 | Margarito et al. |
| 2022/0031254 | A1 | 2/2022 | Al-Ali et al. |
| 2022/0192494 | A1 | 6/2022 | Leabman |
| 2022/0192531 | A1 | 6/2022 | Leabman |
| 2022/0248984 | A1 | 8/2022 | Poeze et al. |

FOREIGN PATENT DOCUMENTS

| | | |
|---|---|---|
| JP | 2012125382 | 7/2012 |
| KR | 1020160081740 | 7/2016 |
| WO | 2017163245 | 9/2017 |
| WO | 2019071138 | 4/2019 |
| WO | 2019217461 | 11/2019 |
| WO | 2020006077 | 1/2020 |
| WO | 2020037171 | 2/2020 |
| WO | 2021198045 A1 | 10/2021 |
| WO | 2022026623 A1 | 2/2022 |

OTHER PUBLICATIONS

"Contributes to longer healthy life expectancy with non-invasive vital acquisition sensor," Quantum Operation Co., Ltd., presentation found on Jan. 12, 2021 at https://oi.nttdata.com/program/forum/history/20191118/pdf/03_quantum-op.pdf (14 pages including English translation).
International Search Report and Written Opinion for PCT/US2019/031176, dated Aug. 23, 2019, 9 pages.
Qiang et al., "Quantitative detection of glucose level based on radiofrequency patch biosensor combined with volume-fixed structures," Biosensors and Bioelectronics 98:357-363, 2017.
Shaker, G. et al., "Non-Invasive Monitoring of Glucose Level Changes Utilizing a mm-Wave Radar System," IJMHCI, vol. 10, Issue 3 (2018): pp. 10-29.
Lien, J. et al., "Soli: Ubiquitous Gesture Sensing with Millimeter Wave Radar," ACM Trans. Graph., vol. 35, No. 4, Article 142, 19 pages (Jul. 2016).
Stojanovic, R. et al., "An optical sensing approach based on light emitting diodes," Journal of Physics: Conference Series 76 (2007), pp. 1-6.
Rossiter, J. et al., "A novel tactile sensor using a matrix of LEDs operating in both photoemitter and photodetector modes," Proc of 4th IEEE International Conference on Sensors (IEEE Sensors 2005), pp. 994-997.
U.S. Appl. No. 17/123,932, titled "Non-Invasive Analyte Sensor and System With Decoupled Transmit and Receive Antennas," filed Dec. 16, 2020 (49 pages).
U.S. Appl. No. 17/123,947, titled "Non-Invasive Detection of an Analyte Using Decoupled Transmit and Receive Antennas," filed Dec. 16, 2020 (46 pages).
U.S. Appl. No. 17/123,961, titled "Non-Invasive Analyte Sensor and System With Decoupled and Inefficient Transmit and Receive Antennas," filed Dec. 16, 2020 (48 pages).
U.S. Appl. No. 17/123,977, titled "Non-Invasive Detection of an Analyte Using Decoupled and Inefficient Transmit and Receive Antennas," filed Dec. 16, 2020 (47 pages).
U.S. Appl. No. 17/123,992, titled "Non-Invasive Analyte Sensor Device," filed Dec. 16, 2020 (47 pages).
U.S. Appl. No. 17/164,073, titled "Analyte Sensor and System With Multiple Detector Lements That Can Transmit or Receive," filed Feb. 1, 2021 (65 pages).
U.S. Appl. No. 17/164,086, titled "Detection of an Analyte Using Multiple Elements That Can Transmit or Receive," filed Feb. 1, 2021 (65 pages).
U.S. Appl. No. 17/164,103, titled "Detection of an Analyte Using Different Combinations of Detector Elements That Can Transmit or Receive," filed Feb. 1, 2021 (65 pages).
U.S. Appl. No. 17/171,281, titled "Non-Invasive Analyte Sensing and Notification System With Decoupled Transmit and Receive Antennas," filed Feb. 9, 2021 (49 pages).
U.S. Appl. No. 17/171,284, titled "Non-Invasive Analyte Sensing and Notification System With Decoupled and Inefficient Transmit and Receive Antennas," filed Feb. 9, 2021 (49 pages).

* cited by examiner

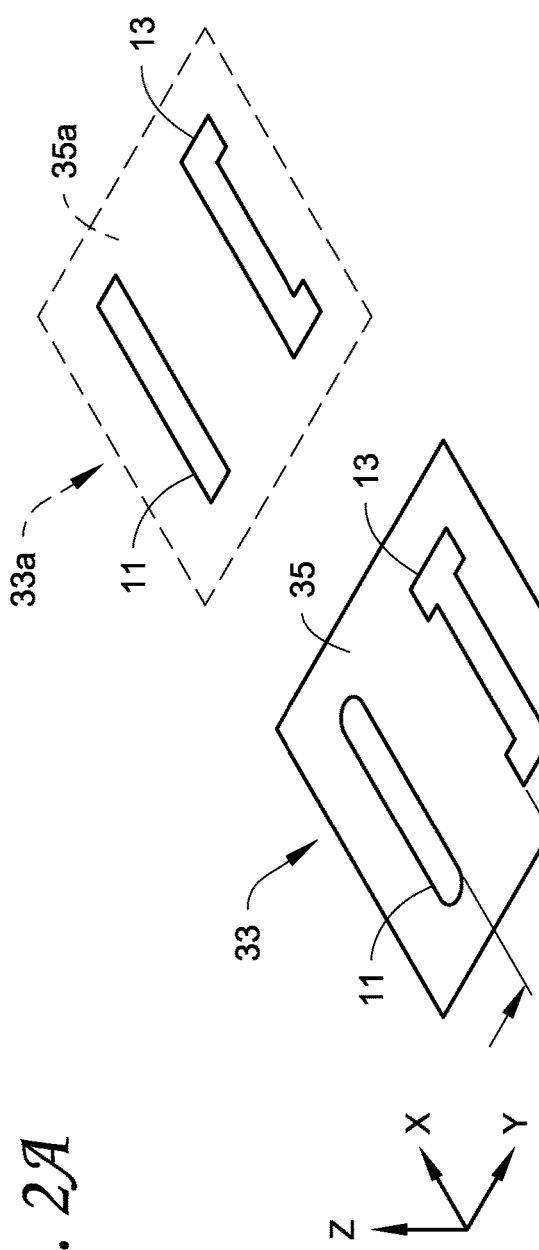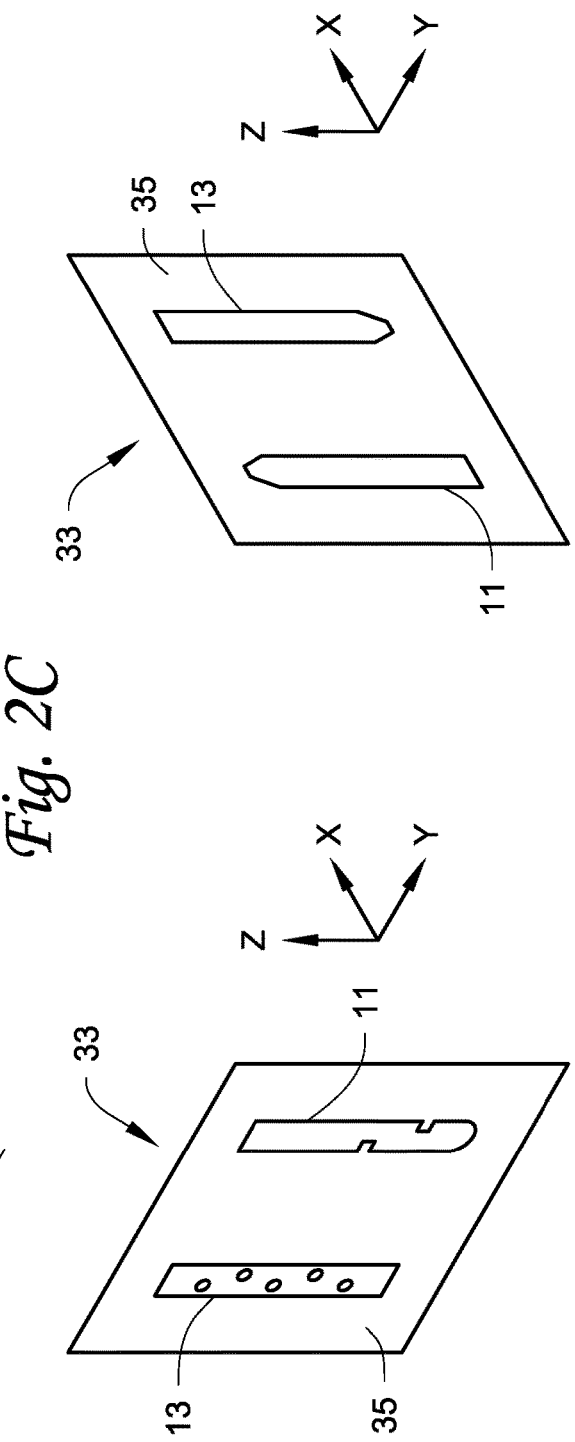

NON-INVASIVE DETECTION OF AN ANALYTE AND NOTIFICATION OF RESULTS

FIELD

This disclosure relates generally to apparatus, systems and methods of non-invasively detecting an analyte via spectroscopic techniques using non-optical frequencies such as in the radio or microwave frequency bands of the electromagnetic spectrum. More specifically, this disclosure relates to non-invasive analyte detection and notification regarding one or more detected analytes.

BACKGROUND

There is interest in being able to detect and/or measure an analyte within a target. One example is measuring glucose in biological tissue. In the example of measuring glucose in a patient, current analyte measurement methods are invasive in that they perform the measurement on a bodily fluid such as blood for fingerstick or laboratory-based tests, or on fluid that is drawn from the patient often using an invasive transcutaneous device. There are non-invasive methods that claim to be able to perform glucose measurements in biological tissues. However, many of the non-invasive methods generally suffer from: lack of specificity to the analyte of interest, such as glucose; interference from temperature fluctuations; interference from skin compounds (i.e. sweat) and pigments; and complexity of placement, i.e. the sensing device resides on multiple locations on the patient's body.

SUMMARY

This disclosure relates generally to apparatus, systems and methods of non-invasively detecting an analyte via spectroscopic techniques using non-optical frequencies such as in the radio or microwave frequency bands of the electromagnetic spectrum. A non-invasive analyte sensor described herein includes at least one transmit antenna (which may also be referred to as a transmit element) that functions to transmit a generated transmit signal in a radio or microwave frequency range of the electromagnetic spectrum into a target containing an analyte of interest, and at least one receive antenna (which may also be referred to as a receive element) that functions to detect a response resulting from transmission of the transmit signal by the transmit antenna into the target.

The transmit and receive antennas are decoupled from one another which helps to improve the detection capability of the non-invasive analyte sensor. The decoupling between the transmit and receive antennas can be achieved using any one or more techniques that causes as much of the signal as possible that is transmitted by the transmit antenna to enter the target and that minimizes or even eliminates the amount of electromagnetic energy that is directly received by the receive antenna from the transmit antenna without traveling into the target. The decoupling can be achieved by one or more intentionally fabricated configurations and/or arrangements between the transmit and receive antennas that is sufficient to decouple the transmit and receive antennas from one another. In one non-limiting embodiment, the decoupling can be achieved by the transmit antenna and the receive antenna having intentionally different geometries from one another. Intentionally different geometries refers to different geometric configurations of the transmit and receive antennas that are intentional, and is distinct from differences in geometry of transmit and receive antennas that may occur by accident or unintentionally, for example due to manufacturing errors or tolerances.

Another technique to achieve decoupling of the transmit and receive antennas is to use an appropriate spacing between each antenna, depending upon factors such as output power, size of the antennas, frequency, and the presence of any shielding, so as to force a proportion of the electromagnetic lines of force of the transmit signal into the target so they reach the analyte, thereby minimizing or eliminating as much as possible direct receipt of electromagnetic energy by the receive antenna directly from the transmit antenna without traveling into the target. This technique helps to ensure that the response detected by the receive antenna is measuring the analyte and is not just the transmitted signal flowing directly from the transmit antenna to the receive antenna. In one embodiment, the sensor can use a first pair of transmit and receive antennas that have a first spacing therebetween, and a second pair of transmit and receive antennas that have a second spacing therebetween that differs from the first spacing.

The techniques described herein can be used to detect the presence of the analyte of interest, as well an amount of the analyte or a concentration of the analyte within the target. The techniques described herein can be used to detect a single analyte or more than one analyte. The target can be any target, for example human or non-human, animal or non-animal, biological or non-biological, that contains the analyte(s) that one may wish to detect. For example, the target can include, but is not limited to, human tissue, animal tissue, plant tissue, an inanimate object, soil, a fluid, genetic material, or a microbe. The analyte(s) can be any analyte, for example human or non-human, animal or non-animal, biological or non-biological, that one may wish to detect. For example, the analyte(s) can include, but is not limited to, one or more of blood glucose, blood alcohol, white blood cells, or luteinizing hormone.

In one embodiment, a method for providing notification regarding one or more analytes can include non-invasively detecting each of the one or more analytes. Detecting each of the one or more analytes can include generating a transmit signal having at least two different frequencies each of which falls within a range of between about 10 kHz to about 100 GHz, transmitting the transmit signal into a target containing at least one analyte of interest from at least one transmit element having a first geometry, and using at least one receive element that is decoupled from the at least one transmit element and having a second geometry that is geometrically different from the first geometry to detect a response resulting from transmitting the transmit signal by the at least one transmit element into the target containing the at least one analyte of interest. The method can further include determining a presence or an amount of each of the one or more analytes based on the response, determining a notification to present based on the presence or amount of at least one of the one or more analytes and notification criteria using a processor, and sending an instruction directing presentation of the notification.

In one embodiment, the method can further include presenting the notification. In one embodiment, presenting the notification includes one or more of producing vibration, producing sound, or displaying a message. In one embodiment, the notification is presented at a device including the non-invasive sensor. In one embodiment, the notification is presented at a device separate from a device including the non-invasive sensor.

In one embodiment, the notification criteria can include a lower threshold value, and the notification to be presented is determined based on whether the amount of one analyte is below the lower threshold value. In one embodiment, the analyte is glucose and the notification is indicative of a low blood sugar condition. In one embodiment, the notification criteria include an upper threshold value, and the notification to be presented is determined based on whether the amount of one of the one or more analytes is above the upper threshold value. In one embodiment, the notification criteria include a lower threshold value and an upper threshold value, and the notification to be presented is determined based on whether the amount of one of the one or more analytes is below the lower threshold value or above the upper threshold value.

In one embodiment, selecting the notification is performed at a device including the non-invasive sensor. In one embodiment, selecting the notification is performed at a device separate from a device separate from a device including the non-invasive sensor. In one embodiment, selecting the notification is performed at a remote server and the notification is presented at a device separate from both a device including the non-invasive sensor and the remote server.

In another embodiment, a method for providing notification regarding one or more analytes can include non-invasively detecting each of the one or more analytes. Detecting each of the one or more analytes can include generating a transmit signal having at least two different frequencies each of which falls within a range of between about 10 kHz to about 100 GHz, transmitting the transmit signal from at least one transmit element having a first geometry into a target containing at least one analyte of interest, and detecting a response resulting from transmitting the transmit signal by the at least one transmit element into the target containing the at least one analyte of interest using at least one receive element that is less than 95% coupled to the at least one transmit element. The method can further include determining a presence or an amount of each of the one or more analytes based on the response, determining a notification to present based on the presence or amount of at least one of the one or more analytes and notification criteria using a processor, and sending an instruction directing presentation of the notification.

In another embodiment, an analyte sensing and notification system includes a non-invasive sensor configured to detect at least one analyte of interest. The non-invasive sensor includes a decoupled antenna array having at least one transmit antenna and at least one receive antenna that are decoupled from one another. The at least one transmit antenna is positioned and arranged to transmit a transmit signal into a target containing the at least one analyte of interest, and the at least one receive antenna is positioned and arranged to detect a response resulting from transmission of the transmit signal by the at least one transmit antenna into the target containing the at least one analyte of interest. The non-invasive sensor further includes a transmit circuit that is electrically connectable to the at least one transmit antenna. The transmit circuit is configured to generate a transmit signal to be transmitted by the at least one transmit antenna. The transmit signal is in a radio or microwave frequency range of the electromagnetic spectrum. The non-invasive sensor further includes a receive circuit that is electrically connectable to the at least one receive antenna, the receive circuit is configured to receive a response detected by the at least one receive antenna. The analyte sensing and notification system further includes a processor configured to determine a notification to present based on detection of the at least one analyte of interest and notification criteria and to send an instruction directing presentation of the notification to present.

In one embodiment, the at least one transmit antenna has a first geometry and the at least one receive antenna has a second geometry that is geometrically different from the first geometry.

In one embodiment, the processor is included in an external device or a remote server, the external device or the remote server separate from the non-invasive sensor. In one embodiment, the processor is a controller included in the non-invasive sensor.

In one embodiment, the analyte sensing and notification system further includes a notification device. In one embodiment, the notification device is included in an external device, the external device separate from the non-invasive sensor. In one embodiment, the notification device is included in the non-invasive sensor.

In another embodiment, the non-invasive sensor configured to detect at least one analyte of interest includes a sensor housing and a decoupled detector array attached to the sensor housing. The decoupled detector array has at least one transmit element and at least one receive element. The at least one transmit element has a first geometry and the at least one receive element has a second geometry that is geometrically different from the first geometry. The at least one transmit element is positioned and arranged to transmit a transmit signal into a target containing the at least one analyte of interest, and the at least one receive element is positioned and arranged to detect a response resulting from transmission of the transmit signal by the at least one transmit element into the target containing the at least one analyte of interest. The at least one transmit element consists of a strip of conductive material having at least one lateral dimension thereof greater than a thickness dimension thereof, and the strip of conductive material of the at least one transmit element is disposed on a substrate. The at least one receive element consists of a strip of conductive material having at least one lateral dimension thereof greater than a thickness dimension thereof, and the strip of conductive material of the at least one receive element is disposed on a substrate. The non-invasive sensor further includes a transmit circuit attached to the sensor housing. The transmit circuit is electrically connectable to the at least one transmit element, the transmit circuit is configured to generate a transmit signal to be transmitted by the at least one transmit element, and the transmit signal is in a radio or microwave frequency range of the electromagnetic spectrum The non-invasive sensor also includes a receive circuit attached to the sensor housing, the receive circuit is electrically connectable to the at least one receive element, the receive circuit is configured to receive a response detected by the at least one receive element.

In another embodiment, the non-invasive sensor configured to detect at least one analyte of interest includes an antenna array having at least one transmit antenna and at least one receive antenna, wherein the at least one transmit antenna and the at least one receive antenna are less than 95% coupled to one another. The non-invasive sensor further includes a transmit circuit that is electrically connectable to the at least one transmit antenna. The transmit circuit is configured to generate a transmit signal to be transmitted by the at least one transmit antenna, the transmit signal is in a radio or microwave frequency range of the electromagnetic spectrum. The non-invasive sensor further includes a receive circuit that is electrically connectable to the at least one receive antenna. The receive circuit is configured to receive a response detected by the at least one receive antenna resulting from transmission of the transmit signal by the at least one transmit antenna into a target containing the at least one analyte of interest.

In another embodiment, the non-invasive sensor configured to detect at least one analyte of interest includes a sensor housing and a decoupled detector array attached to the sensor housing. The decoupled detector array has at least one transmit element and at least one receive element, where the at least one transmit element and the at least one receive element are less than 95% coupled to one another. The at least one transmit element consists of a strip of conductive material having at least one lateral dimension thereof greater than a thickness dimension thereof, the strip of conductive material of the at least one transmit element is disposed on a substrate. The at least one receive element consists of a strip of conductive material having at least one lateral dimension thereof greater than a thickness dimension thereof, the strip of conductive material of the at least one receive element is disposed on a substrate. The non-invasive sensor further includes a transmit circuit attached to the sensor housing. The transmit circuit is electrically connectable to the at least one transmit element. The transmit circuit is configured to generate a transmit signal to be transmitted by the at least one transmit element into a target containing at least one analyte of interest. The transmit signal is in a radio or microwave frequency range of the electromagnetic spectrum. The non-invasive sensor further includes a receive circuit attached to the sensor housing. The receive circuit is electrically connectable to the at least one receive element. The receive circuit is configured to receive a response detected by the at least one receive element resulting from transmission of the transmit signal by the at least one transmit element into the target containing the at least one analyte of interest.

DRAWINGS

References are made to the accompanying drawings that form a part of this disclosure, and which illustrate embodiments in which the apparatus, systems and methods described in this specification can be practiced.

FIG. 1 is a schematic depiction of a non-invasive analyte sensor system with a non-invasive analyte sensor relative to a target according to an embodiment.

FIGS. 2A-C illustrate different example orientations of antenna arrays that can be used in the sensor system described herein.

Like reference numbers represent like parts throughout.

DETAILED DESCRIPTION

Figure 1:
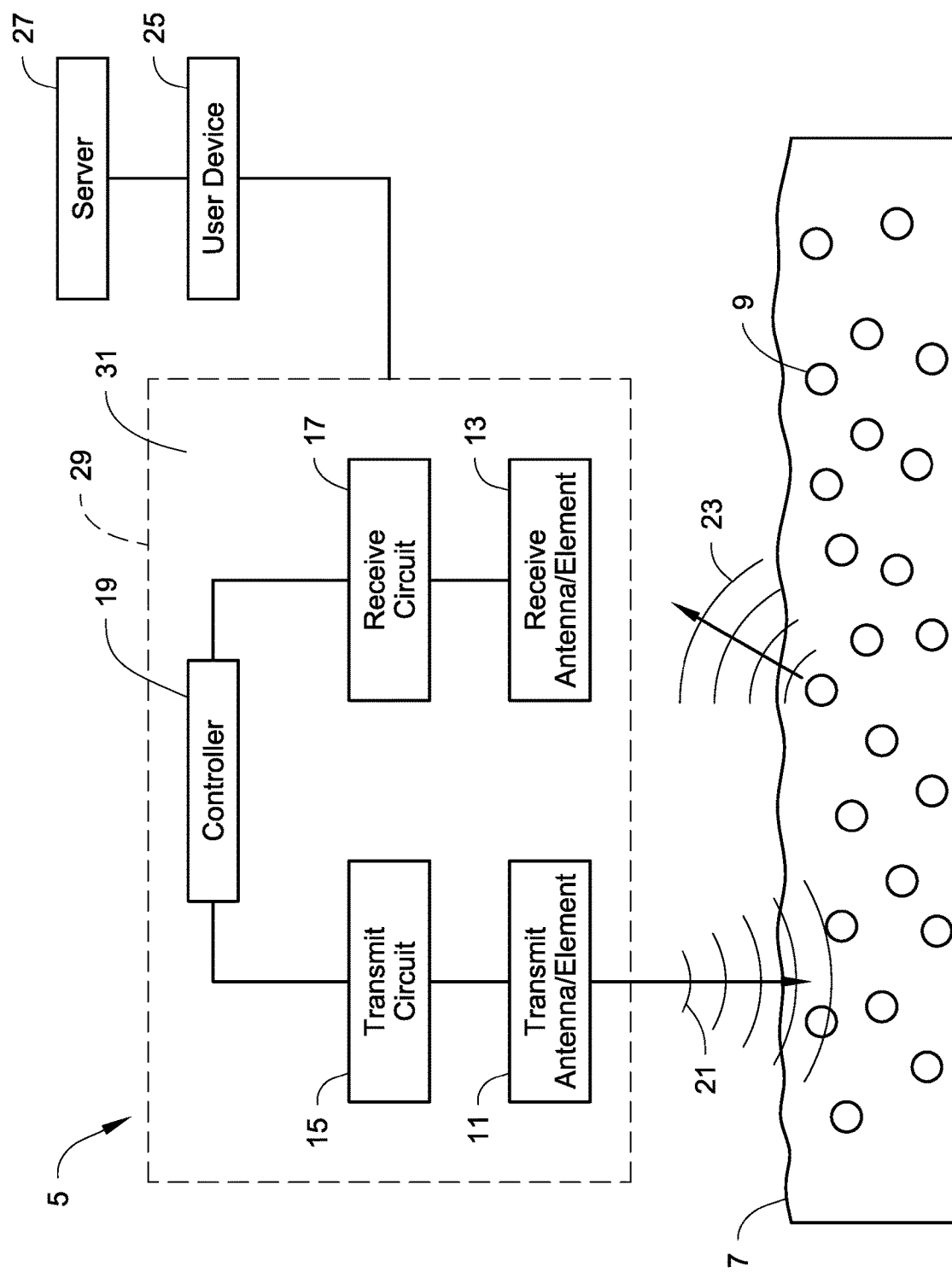

The following is a detailed description of apparatus, systems and methods of non-invasively detecting an analyte via spectroscopic techniques using non-optical frequencies such as in the radio or microwave frequency bands of the electromagnetic spectrum. A non-invasive analyte sensor includes a transmit antenna (which may also be referred to as a transmit element) that functions to transmit a generated transmit signal that is in a radio or microwave frequency range of the electromagnetic spectrum into a target containing an analyte of interest, and a receive antenna (which may also be referred to as a receive element) that functions to detect a response resulting from transmission of the transmit signal by the transmit antenna into the target. The transmit antenna and the receive antenna are decoupled from one another which improves the detection performance of the sensor.

The transmit antenna and the receive antenna can be located near the target and operated as further described herein to assist in detecting at least one analyte in the target. The transmit antenna transmits a signal, which has at least two frequencies in the radio or microwave frequency range, toward and into the target. The signal with the at least two frequencies can be formed by separate signal portions, each having a discrete frequency, that are transmitted separately at separate times at each frequency. In another embodiment, the signal with the at least two frequencies may be part of a complex signal that includes a plurality of frequencies including the at least two frequencies. The complex signal can be generated by blending or multiplexing multiple signals together followed by transmitting the complex signal whereby the plurality of frequencies are transmitted at the same time. One possible technique for generating the complex signal includes, but is not limited to, using an inverse Fourier transformation technique. The receive antenna detects a response resulting from transmission of the signal by the transmit antenna into the target containing the at least one analyte of interest.

The transmit antenna and the receive antenna are decoupled (which may also be referred to as detuned or the like) from one another. Decoupling refers to intentionally fabricating the configuration and/or arrangement of the transmit antenna and the receive antenna to minimize direct communication between the transmit antenna and the receive antenna, preferably absent shielding. Shielding between the transmit antenna and the receive antenna can be utilized. However, the transmit antenna and the receive antenna are decoupled even without the presence of shielding.

The signal(s) detected by the receive antenna can be analyzed to detect the analyte based on the intensity of the received signal(s) and reductions in intensity at one or more frequencies where the analyte absorbs the transmitted signal. An example of detecting an analyte using a non-invasive spectroscopy sensor operating in the radio or microwave frequency range of the electromagnetic spectrum is described in WO 2019/217461, the entire contents of which are incorporated herein by reference. The signal(s) detected by the receive antenna can be complex signals including a plurality of signal components, each signal component being at a different frequency. In an embodiment, the detected complex signals can be decomposed into the signal components at each of the different frequencies, for example through a Fourier transformation. In an embodiment, the complex signal detected by the receive antenna can be analyzed as a whole (i.e. without demultiplexing the complex signal) to detect the analyte as long as the detected signal provides enough information to make the analyte detection. In addition, the signal(s) detected by the receive antenna can be separate signal portions, each having a discrete frequency.

In one embodiment, the sensor described herein can be used to detect the presence of at least one analyte in a target. In another embodiment, the sensor described herein can detect an amount or a concentration of the at least one analyte in the target. The target can be any target containing at least one analyte of interest that one may wish to detect. The target can be human or non-human, animal or non-animal, biological or non-biological. For example, the target can include, but is not limited to, human tissue, animal tissue, plant tissue, an inanimate object, soil, a fluid, genetic material, or a microbe. Non-limiting examples of targets include, but are not limited to, a fluid, for example blood, interstitial fluid, cerebral spinal fluid, lymph fluid or urine, human tissue, animal tissue, plant tissue, an inanimate object, soil, genetic material, or a microbe.

The analyte(s) can be any analyte that one may wish to detect. The analyte can be human or non-human, animal or non-animal, biological or non-biological. For example, the analyte(s) can include, but is not limited to, one or more of blood glucose, blood alcohol, white blood cells, or luteinizing hormone. The analyte(s) can include, but is not limited to, a chemical, a combination of chemicals, a virus, bacteria, or the like. The analyte can be a chemical included in another medium, with non-limiting examples of such media including a fluid containing the at least one analyte, for example blood, interstitial fluid, cerebral spinal fluid, lymph fluid or urine, human tissue, animal tissue, plant tissue, an inanimate object, soil, genetic material, or a microbe. The analyte(s) may also be a non-human, non-biological particle such as a mineral or a contaminant.

The analyte(s) can include, for example, naturally occurring substances, artificial substances, metabolites, and/or reaction products. As non-limiting examples, the at least one analyte can include, but is not limited to, insulin, acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; pro-BNP; BNP; troponin; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, polio virus, *Pseudomonas aeruginosa*, respiratory syncytial virus, *rickettsia* (scrub typhus), *Schistosoma mansoni, Toxoplasma gondii, Trepenoma pallidium, Trypanosoma cruzi*/rangeli, vesicular *stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin.

The analyte(s) can also include one or more chemicals introduced into the target. The analyte(s) can include a marker such as a contrast agent, a radioisotope, or other chemical agent. The analyte(s) can include a fluorocarbon-based synthetic blood. The analyte(s) can include a drug or pharmaceutical composition, with non-limiting examples including ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The analyte(s) can include other drugs or pharmaceutical compositions. The analyte(s) can include neurochemicals or other chemicals generated within the body, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

Referring now to FIG. 1, an embodiment of a non-invasive analyte sensor system with a non-invasive analyte sensor 5 is illustrated. The sensor 5 is depicted relative to a target 7 that contains an analyte of interest 9. In this example, the sensor 5 is depicted as including an antenna array that includes a transmit antenna/element 11 (hereinafter "transmit antenna 11") and a receive antenna/element 13 (hereinafter "receive antenna 13"). The sensor 5 further includes a transmit circuit 15, a receive circuit 17, and a controller 19. As discussed further below, the sensor 5 can also include a power supply, such as a battery (not shown in FIG. 1).

The transmit antenna 11 is positioned, arranged and configured to transmit a signal 21 that is the radio frequency (RF) or microwave range of the electromagnetic spectrum into the target 7. The transmit antenna 11 can be an electrode or any other suitable transmitter of electromagnetic signals in the radio frequency (RF) or microwave range. The transmit antenna 11 can have any arrangement and orientation relative to the target 7 that is sufficient to allow the analyte sensing to take place. In one non-limiting embodiment, the transmit antenna 11 can be arranged to face in a direction that is substantially toward the target 7.

The signal 21 transmitted by the transmit antenna 11 is generated by the transmit circuit 15 which is electrically connectable to the transmit antenna 11. The transmit circuit 15 can have any configuration that is suitable to generate a transmit signal to be transmitted by the transmit antenna 11. Transmit circuits for generating transmit signals in the RF or microwave frequency range are well known in the art. In one embodiment, the transmit circuit 15 can include, for example, a connection to a power source, a frequency generator, and optionally filters, amplifiers or any other suitable elements for a circuit generating an RF or microwave frequency electromagnetic signal. In an embodiment, the signal generated by the transmit circuit 15 can have at least two discrete frequencies (i.e. a plurality of discrete frequencies), each of which is in the range from about 10 kHz to about 100 GHz. In another embodiment, each of the at least two discrete frequencies can be in a range from about 300 MHz to about 6000 MHz. In an embodiment, the transmit circuit 15 can be configured to sweep through a range of frequencies that are within the range of about 10 kHz to about 100 GHz, or in another embodiment a range of about 300 MHz to about 6000 MHz. In an embodiment, the transmit circuit 15 can be configured to produce a complex transmit signal, the complex signal including a plurality of signal components, each of the signal components having a different frequency. The complex signal can be generated by blending or multiplexing multiple signals together followed by transmitting the complex signal whereby the plurality of frequencies are transmitted at the same time.

The receive antenna 13 is positioned, arranged, and configured to detect one or more electromagnetic response signals 23 that result from the transmission of the transmit signal 21 by the transmit antenna 11 into the target 7 and impinging on the analyte 9. The receive antenna 13 can be an electrode or any other suitable receiver of electromagnetic signals in the radio frequency (RF) or microwave range. In an embodiment, the receive antenna 13 is configured to detect electromagnetic signals having at least two frequencies, each of which is in the range from about 10 kHz to about 100 GHz, or in another embodiment a range from about 300 MHz to about 6000 MHz. The receive antenna 13 can have any arrangement and orientation relative to the target 7 that is sufficient to allow detection of the response signal(s) 23 to allow the analyte sensing to take place. In one non-limiting embodiment, the receive antenna 13 can be arranged to face in a direction that is substantially toward the target 7.

The receive circuit 17 is electrically connectable to the receive antenna 13 and conveys the received response from the receive antenna 13 to the controller 19. The receive circuit 17 can have any configuration that is suitable for interfacing with the receive antenna 13 to convert the electromagnetic energy detected by the receive antenna 13 into one or more signals reflective of the response signal(s) 23. The construction of receive circuits are well known in the art. The receive circuit 17 can be configured to condition the signal(s) prior to providing the signal(s) to the controller 19, for example through amplifying the signal(s), filtering the signal(s), or the like. Accordingly, the receive circuit 17 may include filters, amplifiers, or any other suitable components for conditioning the signal(s) provided to the controller 19. In an embodiment, at least one of the receive circuit 17 or the controller 19 can be configured to decompose or demultiplex a complex signal, detected by the receive antenna 13, including a plurality of signal components each at different frequencies into each of the constituent signal components. In an embodiment, decomposing the complex signal can include applying a Fourier transform to the detected complex signal. However, decomposing or demultiplexing a received complex signal is optional. Instead, in an embodiment, the complex signal detected by the receive antenna can be analyzed as a whole (i.e. without demultiplexing the complex signal) to detect the analyte as long as the detected signal provides enough information to make the analyte detection.

The controller 19 controls the operation of the sensor 5. The controller 19, for example, can direct the transmit circuit 15 to generate a transmit signal to be transmitted by the transmit antenna 11. The controller 19 further receives signals from the receive circuit 17. The controller 19 can optionally process the signals from the receive circuit 17 to detect the analyte(s) 9 in the target 7. In one embodiment, the controller 19 may optionally be in communication with at least one external device 25 such as a user device and/or a remote server 27, for example through one or more wireless connections such as Bluetooth, wireless data connections such a 4G, 5G, LTE or the like, or Wi-Fi. If provided, the external device 25 and/or remote server 27 may process (or further process) the signals that the controller 19 receives from the receive circuit 17, for example to detect the analyte(s) 9. If provided, the external device 25 may be used to provide communication between the sensor 5 and the remote server 27, for example using a wired data connection or via a wireless data connection or Wi-Fi of the external device 25 to provide the connection to the remote server 27.

The sensor 5 can further include or be incorporated into a device including notification device 20 configured to provide a human perceptible notification. Notification device 20 can include one or more components for providing the human perceptible notification including, as non-limiting examples, a speaker to provide an audible notification, vibrating components to provide a tactile notification, and/or a light or a display to provide a visual notification. In an embodiment, the sensor 5 can direct presentation of the notification based on the presence or amount of the analyte 9 and notification criteria. In an embodiment, the sensor 5 or device that sensor 5 is incorporated into can be directed to present the notification by external device 25 or remote server 27. In an embodiment, the sensor 5 includes a processor configured to determine a notification to be presented and send an instruction directing presentation of the notification to be presented. In an embodiment, controller 19 of sensor 5 can be configured to determine a notification to present and send an instruction directing presentation of the notification.

The external device 25 can be, as non-limiting examples, a mobile phone (a.k.a. cell phone, smartphone); a tablet computer; a laptop computer; a personal computer; a wearable device such as a watch or a head-mounted device or clothing; a video game console; furniture such as a chair; a vehicle such as a car, automobile or truck; lightbulbs; smart home appliances such as a smart refrigerator; and a use specific device similar to these devices that is specifically designed to function with the sensor 5. In an embodiment, the external device 25 can present a notification. In an embodiment, presentation of a notification is determined at the external device 25 based on notification criteria and a presence or amount of analyte 9 that is detected. In an embodiment, the external device 25 can direct the sensor 5 to provide the notification. In an embodiment, the external device 25 can be directed to provide the notification by sensor 5 or remote server 27. The external device 25 can include a notification device 30 configured to provide a human perceptible notification. Notification device 30 can include one or more components for providing the human perceptible notification including, as non-limiting examples, a speaker to provide an audible notification, vibrating components to provide a tactile notification, and/or a light or a display to provide a visual notification. In an embodiment, the external device 25 includes a processor 26 configured to determine a notification to present and send an instruction directing presentation of the notification.

The remote server 27 can be configured to determine presentation of a notification based on a presence or amount of the analyte 9 that is detected, for example using notification criteria as described below. The remote server 27 can direct one or both of the sensor 5 or external device 25 to present the notification, for example by sending a command or other such message through the connection linking remote server 27 to sensor 5 or external device 25. In an embodiment, the remote server 27 includes a processor 28 configured to determine a notification to present and send an instruction directing presentation of the notification.

With continued reference to FIG. 1, the sensor 5 may include a sensor housing 29 (shown in dashed lines) that defines an interior space 31. Components of the sensor 5 may be attached to and/or disposed within the housing 29. For example, the transmit antenna 11 and the receive antenna 13 are attached to the housing 29. In some embodiments, the antennas 11, 13 may be entirely or partially within the interior space 31 of the housing 29. In some embodiments, the antennas 11, 13 may be attached to the housing 29 but at least partially or fully located outside the interior space 31. In some embodiments, the transmit circuit 15, the receive circuit 17 and the controller 19 are attached to the housing 29 and disposed entirely within the sensor housing 29.

The receive antenna 13 is decoupled or detuned with respect to the transmit antenna 11 such that electromagnetic coupling between the transmit antenna 11 and the receive antenna 13 is reduced. The decoupling of the transmit antenna 11 and the receive antenna 13 increases the portion of the signal(s) detected by the receive antenna 13 that is the response signal(s) 23 from the target 7, and minimizes direct receipt of the transmitted signal 21 by the receive antenna 13. The decoupling of the transmit antenna 11 and the receive antenna 13 results in transmission from the transmit antenna 11 to the receive antenna 13 having a reduced forward gain (S21) and an increased reflection at output (S22) compared to antenna systems having coupled transmit and receive antennas.

In an embodiment, coupling between the transmit antenna 11 and the receive antenna 13 is 95% or less. In another embodiment, coupling between the transmit antenna 11 and the receive antenna 13 is 90% or less. In another embodiment, coupling between the transmit antenna 11 and the receive antenna 13 is 85% or less. In another embodiment, coupling between the transmit antenna 11 and the receive antenna 13 is 75% or less.

Any technique for reducing coupling between the transmit antenna 11 and the receive antenna 13 can be used. For example, the decoupling between the transmit antenna 11 and the receive antenna 13 can be achieved by one or more intentionally fabricated configurations and/or arrangements between the transmit antenna 11 and the receive antenna 13 that is sufficient to decouple the transmit antenna 11 and the receive antenna 13 from one another.

For example, in one embodiment described further below, the decoupling of the transmit antenna 11 and the receive antenna 13 can be achieved by intentionally configuring the transmit antenna 11 and the receive antenna 13 to have different geometries from one another. Intentionally different geometries refers to different geometric configurations of the transmit and receive antennas 11, 13 that are intentional. Intentional differences in geometry are distinct from differences in geometry of transmit and receive antennas that may occur by accident or unintentionally, for example due to manufacturing errors or tolerances.

Another technique to achieve decoupling of the transmit antenna 11 and the receive antenna 13 is to provide appropriate spacing between each antenna 11, 13 that is sufficient to decouple the antennas 11, 13 and force a proportion of the electromagnetic lines of force of the transmitted signal 21 into the target 7 thereby minimizing or eliminating as much as possible direct receipt of electromagnetic energy by the receive antenna 13 directly from the transmit antenna 11 without traveling into the target 7. The appropriate spacing between each antenna 11, 13 can be determined based upon factors that include, but are not limited to, the output power of the signal from the transmit antenna 11, the size of the antennas 11, 13, the frequency or frequencies of the transmitted signal, and the presence of any shielding between the antennas. This technique helps to ensure that the response detected by the receive antenna 13 is measuring the analyte 9 and is not just the transmitted signal 21 flowing directly from the transmit antenna 11 to the receive antenna 13. In some embodiments, the appropriate spacing between the antennas 11, 13 can be used together with the intentional difference in geometries of the antennas 11, 13 to achieve decoupling.

In one embodiment, the transmit signal that is transmitted by the transmit antenna 11 can have at least two different frequencies, for example upwards of 7 to 12 different and discrete frequencies. In another embodiment, the transmit signal can be a series of discrete, separate signals with each separate signal having a single frequency or multiple different frequencies.

In one embodiment, the transmit signal (or each of the transmit signals) can be transmitted over a transmit time that is less than, equal to, or greater than about 300 ms. In another embodiment, the transmit time can be than, equal to, or greater than about 200 ms. In still another embodiment, the transmit time can be less than, equal to, or greater than about 30 ms. The transmit time could also have a magnitude that is measured in seconds, for example 1 second, 5 seconds, 10 seconds, or more. In an embodiment, the same transmit signal can be transmitted multiple times, and then the transmit time can be averaged. In another embodiment, the transmit signal (or each of the transmit signals) can be transmitted with a duty cycle that is less than or equal to about 50%.

FIGS. 2A-2C illustrate examples of antenna arrays 33 that can be used in the sensor system 5 and how the antenna arrays 33 can be oriented. Many orientations of the antenna arrays 33 are possible, and any orientation can be used as long as the sensor 5 can perform its primary function of sensing the analyte 9.

In FIG. 2A, the antenna array 33 includes the transmit antenna 11 and the receive antenna 13 disposed on a substrate 35 which may be substantially planar. This example depicts the array 33 disposed substantially in an X-Y plane. In this example, dimensions of the antennas 11, 13 in the X and Y-axis directions can be considered lateral dimensions, while a dimension of the antennas 11, 13 in the Z-axis direction can be considered a thickness dimension. In this example, each of the antennas 11, 13 has at least one lateral dimension (measured in the X-axis direction and/or in the Y-axis direction) that is greater than the thickness dimension thereof (in the Z-axis direction). In other words, the transmit antenna 11 and the receive antenna 13 are each relatively flat or of relatively small thickness in the Z-axis direction compared to at least one other lateral dimension measured in the X-axis direction and/or in the Y-axis direction.

In use of the embodiment in FIG. 2A, the sensor and the array 33 may be positioned relative to the target 7 such that the target 7 is below the array 33 in the Z-axis direction or above the array 33 in the Z-axis direction whereby one of the faces of the antennas 11, 13 face toward the target 7. Alternatively, the target 7 can be positioned to the left or right sides of the array 33 in the X-axis direction whereby one of the ends of each one of the antennas 11, 13 face toward the target 7. Alternatively, the target 7 can be positioned to the sides of the array 33 in the Y-axis direction whereby one of the sides of each one of the antennas 11, 13 face toward the target 7.

The sensor 5 can also be provided with one or more additional antenna arrays in addition the antenna array 33. For example, FIG. 2A also depicts an optional second antenna array 33a that includes the transmit antenna 11 and the receive antenna 13 disposed on a substrate 35a which may be substantially planar. Like the array 33, the array 33a may also be disposed substantially in the X-Y plane, with the arrays 33, 33a spaced from one another in the X-axis direction.

In FIG. 2B, the antenna array 33 is depicted as being disposed substantially in the Y-Z plane. In this example, dimensions of the antennas 11, 13 in the Y and Z-axis directions can be considered lateral dimensions, while a dimension of the antennas 11, 13 in the X-axis direction can be considered a thickness dimension. In this example, each of the antennas 11, 13 has at least one lateral dimension (measured in the Y-axis direction and/or in the Z-axis direction) that is greater than the thickness dimension thereof (in the X-axis direction). In other words, the transmit antenna 11 and the receive antenna 13 are each relatively flat or of relatively small thickness in the X-axis direction compared to at least one other lateral dimension measured in the Y-axis direction and/or in the Z-axis direction.

In use of the embodiment in FIG. 2B, the sensor and the array 33 may be positioned relative to the target 7 such that the target 7 is below the array 33 in the Z-axis direction or above the array 33 in the Z-axis direction whereby one of the ends of each one of the antennas 11, 13 face toward the target 7. Alternatively, the target 7 can be positioned in front of or behind the array 33 in the X-axis direction whereby one of the faces of each one of the antennas 11, 13 face toward the target 7. Alternatively, the target 7 can be positioned to one of the sides of the array 33 in the Y-axis direction whereby one of the sides of each one of the antennas 11, 13 face toward the target 7.

In FIG. 2C, the antenna array 33 is depicted as being disposed substantially in the X-Z plane. In this example, dimensions of the antennas 11, 13 in the X and Z-axis directions can be considered lateral dimensions, while a dimension of the antennas 11, 13 in the Y-axis direction can be considered a thickness dimension. In this example, each of the antennas 11, 13 has at least one lateral dimension (measured in the X-axis direction and/or in the Z-axis direction) that is greater than the thickness dimension thereof (in the Y-axis direction). In other words, the transmit antenna 11 and the receive antenna 13 are each relatively flat or of relatively small thickness in the Y-axis direction compared to at least one other lateral dimension measured in the X-axis direction and/or in the Z-axis direction.

In use of the embodiment in FIG. 2C, the sensor and the array 33 may be positioned relative to the target 7 such that the target 7 is below the array 33 in the Z-axis direction or above the array 33 in the Z-axis direction whereby one of the ends of each one of the antennas 11, 13 face toward the target 7. Alternatively, the target 7 can be positioned to the left or right sides of the array 33 in the X-axis direction whereby one of the sides of each one of the antennas 11, 13 face toward the target 7. Alternatively, the target 7 can be positioned in front of or in back of the array 33 in the Y-axis direction whereby one of the faces of each one of the antennas 11, 13 face toward the target 7.

The arrays 33, 33a in FIGS. 2A-2C need not be oriented entirely within a plane such as the X-Y plane, the Y-Z plane or the X-Z plane. Instead, the arrays 33, 33a can be disposed at angles to the X-Y plane, the Y-Z plane and the X-Z plane.

Decoupling Antennas Using Differences in Antenna Geometries

As mentioned above, one technique for decoupling the transmit antenna 11 from the receive antenna 13 is to intentionally configure the transmit antenna 11 and the receive antenna 13 to have intentionally different geometries. Intentionally different geometries refers to differences in geometric configurations of the transmit and receive antennas 11, 13 that are intentional, and is distinct from differences in geometry of the transmit and receive antennas 11, 13 that may occur by accident or unintentionally, for example due to manufacturing errors or tolerances when fabricating the antennas 11, 13.

The different geometries of the antennas 11, 13 may manifest itself, and may be described, in a number of different ways. For example, in a plan view of each of the antennas 11, 13 (such as in FIGS. 3A-I), the shapes of the perimeter edges of the antennas 11, 13 may be different from one another. The different geometries may result in the antennas 11, 13 having different surface areas in plan view. The different geometries may result in the antennas 11, 13 having different aspect ratios in plan view (i.e. a ratio of their sizes in different dimensions; for example, as discussed in further detail below, the ratio of the length divided by the width of the antenna 11 may be different than the ratio of the length divided by the width for the antenna 13). In some embodiments, the different geometries may result in the antennas 11, 13 having any combination of different perimeter edge shapes in plan view, different surface areas in plan view, and/or different aspect ratios. In some embodiments, the antennas 11, 13 may have one or more holes formed therein (see FIG. 2B) within the perimeter edge boundary, or one or more notches formed in the perimeter edge (see FIG. 2B).

So as used herein, a difference in geometry or a difference in geometrical shape of the antennas 11, 13 refers to any intentional difference in the figure, length, width, size, shape, area closed by a boundary (i.e. the perimeter edge), etc. when the respective antenna 11, 13 is viewed in a plan view.

The antennas 11, 13 can have any configuration and can be formed from any suitable material that allows them to perform the functions of the antennas 11, 13 as described herein. In one embodiment, the antennas 11, 13 can be formed by strips of material. A strip of material can include a configuration where the strip has at least one lateral dimension thereof greater than a thickness dimension thereof when the antenna is viewed in a plan view (in other words, the strip is relatively flat or of relatively small thickness compared to at least one other lateral dimension, such as length or width when the antenna is viewed in a plan view as in FIGS. 3A-I). A strip of material can include a wire. The antennas 11, 13 can be formed from any suitable conductive material(s) including metals and conductive non-metallic materials. Examples of metals that can be used include, but are not limited to, copper or gold. Another example of a material that can be used is non-metallic materials that are doped with metallic material to make the non-metallic material conductive.

In FIGS. 2A-2C, the antennas 11, 13 within each one of the arrays 33, 33a have different geometries from one another. In addition, FIGS. 3A-I illustrate plan views of additional examples of the antennas 11, 13 having different geometries from one another. The examples in FIGS. 2A-2C and 3A-I are not exhaustive and many different configurations are possible.

Figure 3A:
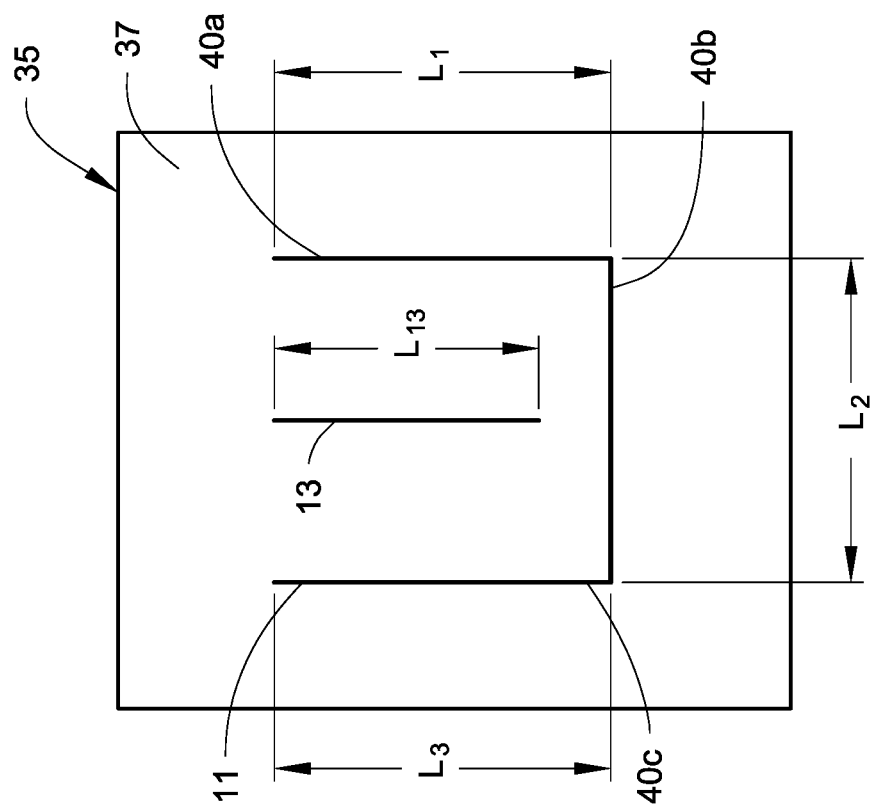
FIGS. 3A-3I illustrate different examples of transmit and receive antennas with different geometries.

With reference initially to FIG. 3A, a plan view of an antenna array having two antennas with different geometries is illustrated. In this example (as well as for the examples in FIGS. 2A-2C and 3B-3I), for sake of convenience in describing the concepts herein, one antenna is labeled as the transmit antenna 11 and the other antenna is labeled as the receive antenna 13. However, the antenna labeled as the transmit antenna 11 could be the receive antenna 13, while the antenna labeled as the receive antenna 13 could be the transmit antenna 11. Each of the antennas 11, 13 are disposed on the substrate 35 having a planar surface 37.

The antennas 11, 13 can be formed as linear strips or traces on the surface 37. In this example, the antenna 11 is generally U-shaped and has a first linear leg 40a, a second linear leg 40b that extends perpendicular to the first leg 40a, and a third linear leg 40c that extends parallel to the leg 40a. Likewise, the antenna 13 is formed by a single leg that extends parallel to, and between, the legs 40a, 40c.

In the example depicted in FIG. 3A, each one of the antennas 11, 13 has at least one lateral dimension that is greater than a thickness dimension thereof (in FIG. 3A, the thickness dimension would extend into/from the page when viewing FIG. 3A). For example, the leg 40a of the antenna 11 extends in one direction (i.e. a lateral dimension) an extent that is greater than a thickness dimension of the leg 40a extending into or out of the page; the leg 40b of the antenna 11 extends in a direction (i.e. a lateral dimension) an extent that is greater than a thickness dimension of the leg 40b extending into or out of the page; and the leg 40c of the antenna 11 extends in one direction (i.e. a lateral dimension) an extent that is greater than a thickness dimension of the leg 40c extending into or out of the page. Likewise, the antenna 13 extends in one direction (i.e. a lateral dimension) an extent that is greater than a thickness dimension of the antenna 13 extending into or out of the page.

The antennas 11, 13 also differ in geometry from one another in that the total linear length of the antenna 11 (determined by adding the individual lengths $L_1$, $L_2$, $L_3$ of the legs 40a-c together) when viewed in plan view is greater than the length $L_{13}$ of the antenna 13 when viewed in plan view.

Figure 3B:
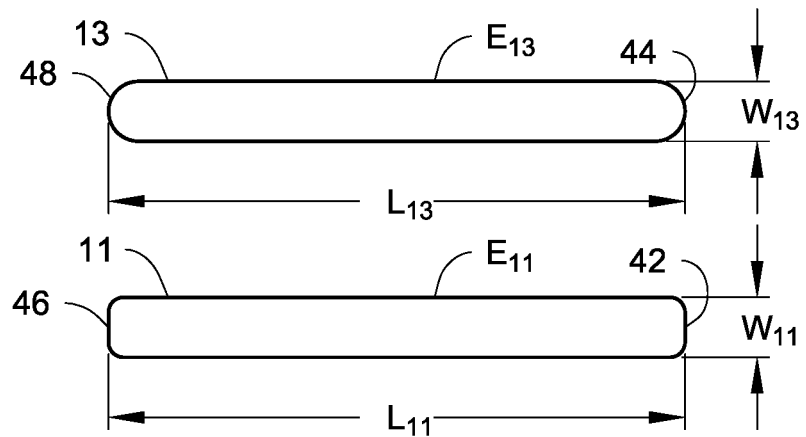

FIG. 3B illustrates another plan view of an antenna array having two antennas with different geometries. In this example, the antennas 11, 13 are illustrated as substantially linear strips each with a lateral length $L_{11}$, $L_{13}$, a lateral width $W_{11}$, $W_{13}$, and a perimeter edge $E_{11}$, $E_{13}$. The perimeter edges $E_{11}$, $E_{13}$ extend around the entire periphery of the antennas 11, 13 and bound an area in plan view. In this example, the lateral length $L_{11}$, $L_{13}$ and/or the lateral width $W_{11}$, $W_{13}$ is greater than a thickness dimension of the antennas 11, 13 extending into/from the page when viewing FIG. 3B. In this example, the antennas 11, 13 differ in geometry from one another in that the shapes of the ends of the antennas 11, 13 differ from one another. For example, when viewing FIG. 3B, the right end 42 of the antenna 11 has a different shape than the right end 44 of the antenna 13. Similarly, the left end 46 of the antenna 11 may have a similar shape as the right end 42, but differs from the left end 48 of the antenna 13 which may have a similar shape as the right end 44. It is also possible that the lateral lengths $L_{11}$, $L_{13}$ and/or the lateral widths $W_{11}$, $W_{13}$ of the antennas 11, 13 could differ from one another.

Figure 3C:
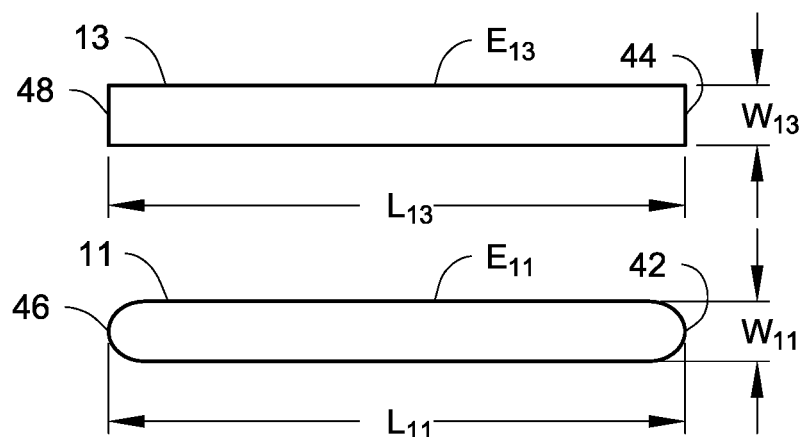

FIG. 3C illustrates another plan view of an antenna array having two antennas with different geometries that is somewhat similar to FIG. 3B. In this example, the antennas 11, 13 are illustrated as substantially linear strips each with the lateral length $L_{11}$, $L_{13}$, the lateral width $W_{11}$, $W_{13}$, and the perimeter edge $E_{11}$, $E_{13}$. The perimeter edges $E_{11}$, $E_{13}$ extend around the entire periphery of the antennas 11, 13 and bound an area in plan view. In this example, the lateral length $L_{11}$, $L_{13}$ and/or the lateral width $W_{11}$, $W_{13}$ is greater than a thickness dimension of the antennas 11, 13 extending into/from the page when viewing FIG. 3C. In this example, the antennas 11, 13 differ in geometry from one another in that the shapes of the ends of the antennas 11, 13 differ from one another. For example, when viewing FIG. 3C, the right end 42 of the antenna 11 has a different shape than the right end 44 of the antenna 13. Similarly, the left end 46 of the antenna 11 may have a similar shape as the right end 42, but differs from the left end 48 of the antenna 13 which may have a similar shape as the right end 44. In addition, the lateral widths $W_{11}$, $W_{13}$ of the antennas 11, 13 differ from one another. It is also possible that the lateral lengths $L_{11}$, $L_{13}$ of the antennas 11, 13 could differ from one another.

Figure 3D:
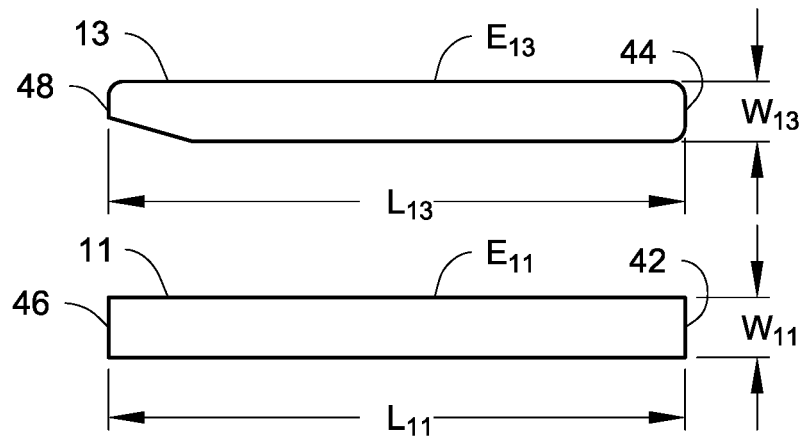

FIG. 3D illustrates another plan view of an antenna array having two antennas with different geometries that is somewhat similar to FIGS. 3B and 3C. In this example, the antennas 11, 13 are illustrated as substantially linear strips each with the lateral length $L_{11}$, $L_{13}$, the lateral width $W_{11}$, $W_{13}$, and the perimeter edge $E_{11}$, $E_{13}$. The perimeter edges $E_{11}$, $E_{13}$ extend around the entire periphery of the antennas 11, 13 and bound an area in plan view. In this example, the lateral length $L_{11}$, $L_{13}$ and/or the lateral width $W_{11}$, $W_{13}$ is greater than a thickness dimension of the antennas 11, 13 extending into/from the page when viewing FIG. 3D. In this example, the antennas 11, 13 differ in geometry from one another in that the shapes of the ends of the antennas 11, 13 differ from one another. For example, when viewing FIG. 3D, the right end 42 of the antenna 11 has a different shape than the right end 44 of the antenna 13. Similarly, the left end 46 of the antenna 11 may have a similar shape as the right end 42, but differs from the left end 48 of the antenna 13 which may have a similar shape as the right end 44. In addition, the lateral widths $W_{11}$, $W_{13}$ of the antennas 11, 13 differ from one another. It is also possible that the lateral lengths $L_{11}$, $L_{13}$ of the antennas 11, 13 could differ from one another.

Figure 3F:
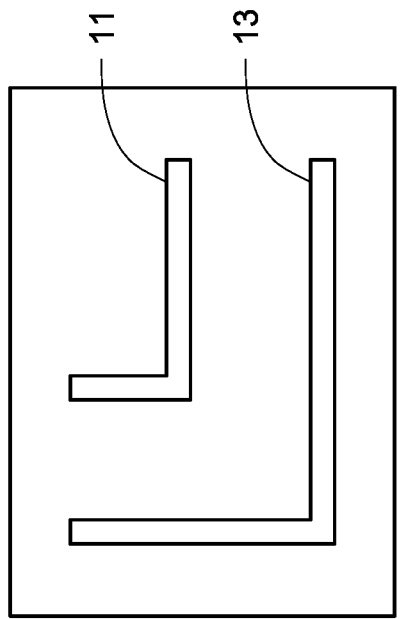
Figure 3G:
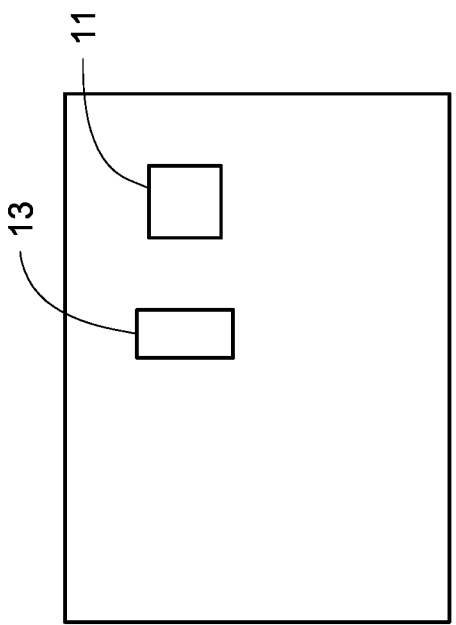
Figure 3E:
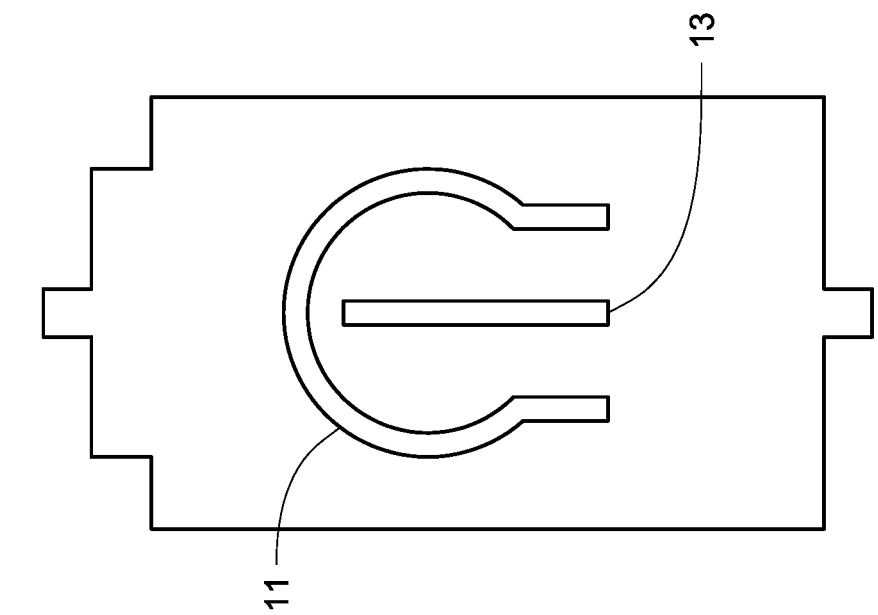

FIG. 3E illustrates another plan view of an antenna array having two antennas with different geometries on a substrate. In this example, the antenna 11 is illustrated as being a strip of material having a generally horseshoe shape, while the antenna 13 is illustrated as being a strip of material that is generally linear. The planar shapes (i.e. geometries) of the antennas 11, 13 differ from one another. In addition, the total length of the antenna 11 (measured from one end to the other) when viewed in plan view is greater than the length of the antenna 13 when viewed in plan.

FIG. 3F illustrates another plan view of an antenna array having two antennas with different geometries on a substrate. In this example, the antenna 11 is illustrated as being a strip of material forming a right angle, and the antenna 13 is also illustrated as being a strip of material that forms a larger right angle. The planar shapes (i.e. geometries) of the antennas 11, 13 differ from one another since the total area in plan view of the antenna 13 is greater than the total area in plan view of the antenna 11. In addition, the total length of the antenna 11 (measured from one end to the other) when viewed in plan view is less than the length of the antenna 13 when viewed in plan.

FIG. 3G illustrates another plan view of an antenna array having two antennas with different geometries on a substrate. In this example, the antenna 11 is illustrated as being a strip of material forming a square, and the antenna 13 is illustrated as being a strip of material that forms a rectangle. The planar shapes (i.e. geometries) of the antennas 11, 13 differ from one another. In addition, at least one of the width/length of the antenna 11 when viewed in plan view is less than one of the width/length of the antenna 13 when viewed in plan.

Figure 3I:
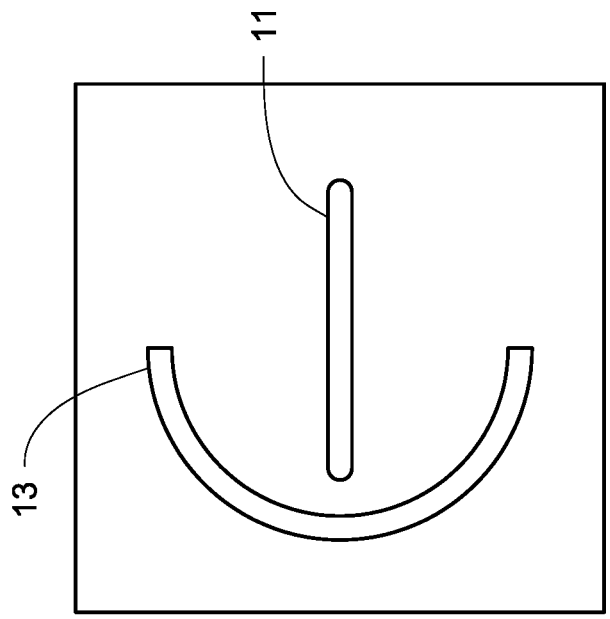
Figure 3H:
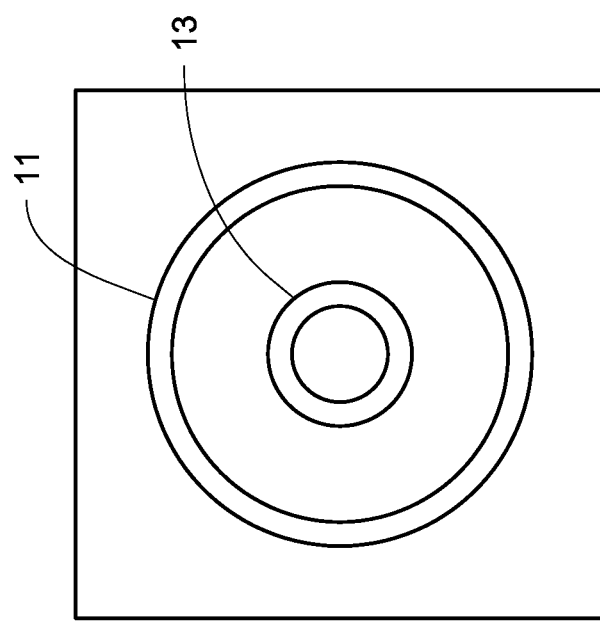

FIG. 3H illustrates another plan view of an antenna array having two antennas with different geometries on a substrate. In this example, the antenna 11 is illustrated as being a strip of material forming a circle when viewed in plan, and the antenna 13 is also illustrated as being a strip of material that forms a smaller circle when viewed in plan surrounded by the circle formed by the antenna 11. The planar shapes (i.e. geometries) of the antennas 11, 13 differ from one another due to the different sizes of the circles.

FIG. 3I illustrates another plan view of an antenna array having two antennas with different geometries on a substrate. In this example, the antenna 11 is illustrated as being a linear strip of material, and the antenna 13 is illustrated as being a strip of material that forms a semi-circle when viewed in plan. The planar shapes (i.e. geometries) of the antennas 11, 13 differ from one another due to the different shapes/geometries of the antennas 11, 13.

Figure 4A:
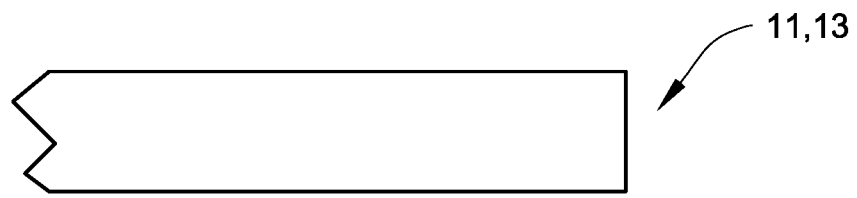
FIGS. 4A, 4B, 4C and 4D illustrate additional examples of different shapes that the ends of the transmit and receive antennas can have.
Figure 4B:
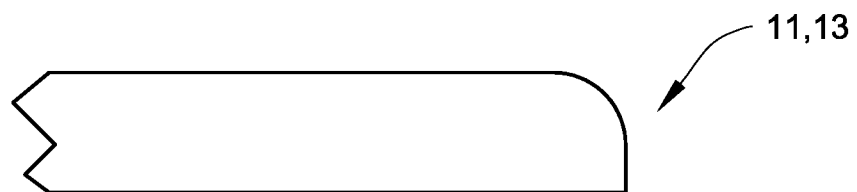
Figure 4C:
Figure 4D:
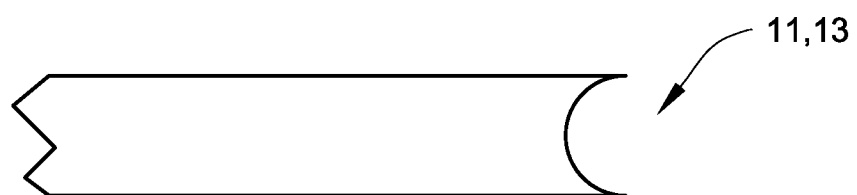

4A-D are plan views of additional examples of different shapes that the ends of the transmit and receive antennas 11, 13 can have to achieve differences in geometry. Either one of, or both of, the ends of the antennas 11, 13 can have the shapes in FIGS. 4A-D, including in the embodiments in FIGS. 3A-I. FIG. 4A depicts the end as being generally rectangular. FIG. 4B depicts the end as having one rounded corner while the other corner remains a right angle. FIG. 4C depicts the entire end as being rounded or outwardly convex. FIG. 4D depicts the end as being inwardly concave. Many other shapes are possible.

Another technique to achieve decoupling of the antennas 11, 13 is to use an appropriate spacing between each antenna 11, 13 with the spacing being sufficient to force most or all of the signal(s) transmitted by the transmit antenna 11 into the target, thereby minimizing the direct receipt of electromagnetic energy by the receive antenna 13 directly from the transmit antenna 11. The appropriate spacing can be used by itself to achieve decoupling of the antennas 11, 13. In another embodiment, the appropriate spacing can be used together with differences in geometry of the antennas 11, 13 to achieve decoupling.

Referring to FIG. 2A, there is a spacing D between the transmit antenna 11 and the receive antenna 13 at the location indicated. The spacing D between the antennas 11, 13 may be constant over the entire length (for example in the X-axis direction) of each antenna 11, 13, or the spacing D between the antennas 11, 13 could vary. Any spacing D can be used as long as the spacing D is sufficient to result in most or all of the signal(s) transmitted by the transmit antenna 11 reaching the target and minimizing the direct receipt of electromagnetic energy by the receive antenna 13 directly from the transmit antenna 11, thereby decoupling the antennas 11, 13 from one another.

Figure 5:
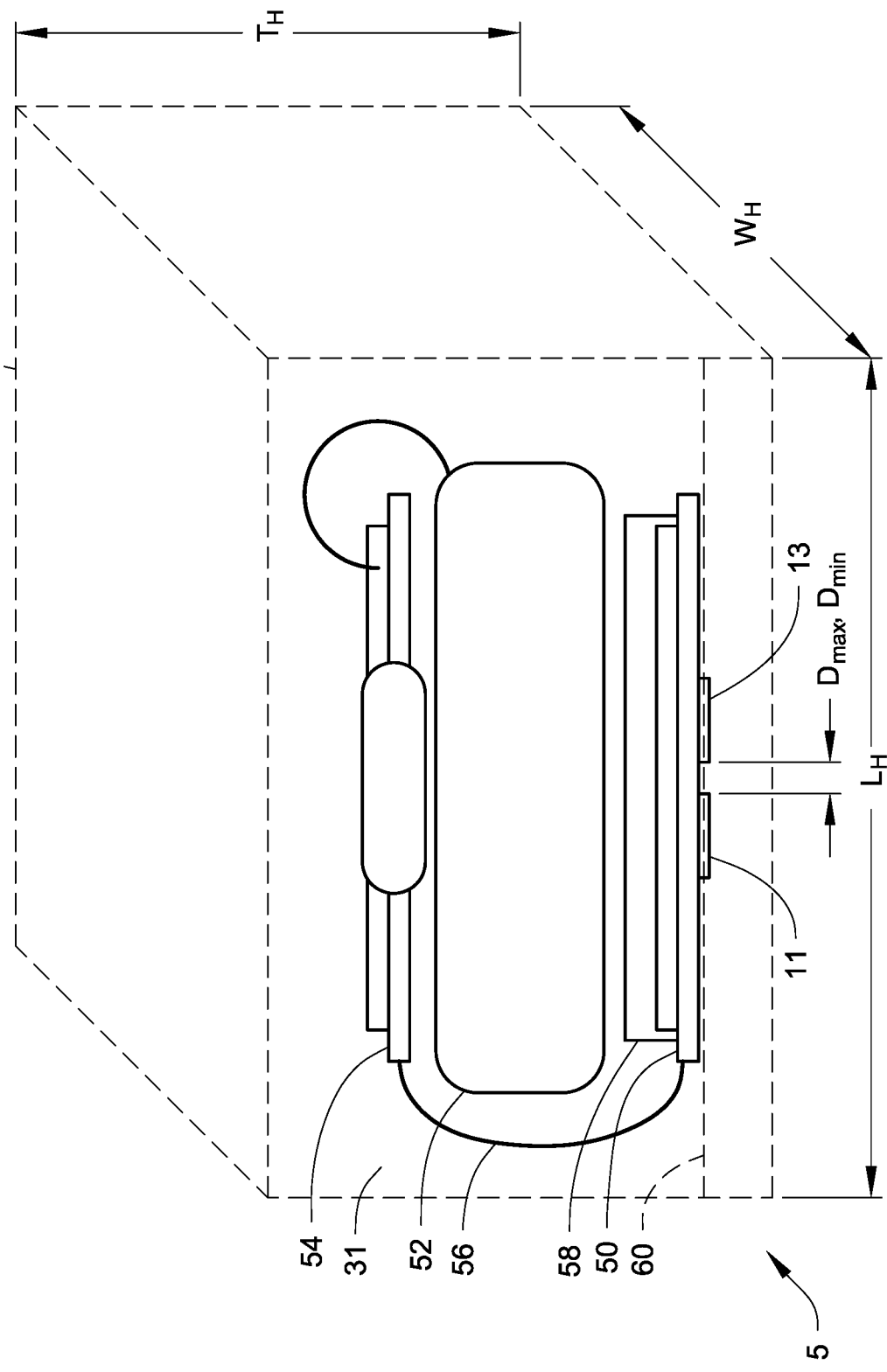
FIG. 5 is a schematic depiction of a sensor device according to an embodiment.

Referring to FIG. 5, an example configuration of the sensor device 5 is illustrated. In FIG. 5, elements that are identical or similar to elements in FIG. 1 are referenced using the same reference numerals. In FIG. 5, the antennas 11, 13 are disposed on one surface of a substrate 50 which can be, for example, a printed circuit board. At least one battery 52, such as a rechargeable battery, is provided above the substrate 50, for providing power to the sensor device 5. In addition, a digital printed circuit board 54 is provided on which the transmit circuit 15, the receive circuit 17, and the controller 19 and other electronics of the second device 5 can be disposed. The substrate 50 and the digital printed circuit board 54 are electrically connected via any suitable electrical connection, such as a flexible connector 56. An RF shield 58 may optionally be positioned between the antennas 11, 13 and the battery 52, or between the antennas 11, 13 and the digital printed circuit board 54, to shield the circuitry and electrical components from RF interference.

As depicted in FIG. 5, all of the elements of the sensor device 5, including the antennas 11, 13, the transmit circuit 15, the receive circuit 17, the controller 19, the battery 52 and the like are contained entirely within the interior space 31 of the housing 29. In an alternative embodiment, a portion of or the entirety of each antenna 11, 13 can project below a bottom wall 60 of the housing 29. In another embodiment, the bottom of each antenna 11, 13 can be level with the bottom wall 60, or they can be slightly recessed from the bottom wall 60.

The housing 29 of the sensor device 5 can have any configuration and size that one finds suitable for employing in a non-invasive sensor device. In one embodiment, the housing 29 can have a maximum length dimension $L_H$ no greater than 50 mm, a maximum width dimension $W_H$ no greater than 50 mm, and a maximum thickness dimension $T_H$ no greater than 25 mm, for a total interior volume of no greater than about 62.5 cm$^3$.

In addition, with continued reference to FIG. 5 together with FIGS. 3A-3I, there is preferably a maximum spacing $D_{max}$ and a minimum spacing $D_{min}$ between the transmit antenna 11 and the receive antenna 13. The maximum spacing $D_{max}$ may be dictated by the maximum size of the housing 29. In one embodiment, the maximum spacing $D_{max}$ can be about 50 mm. In one embodiment, the minimum spacing $D_{min}$ can be from about 1.0 mm to about 5.0 mm.

Figure 6:
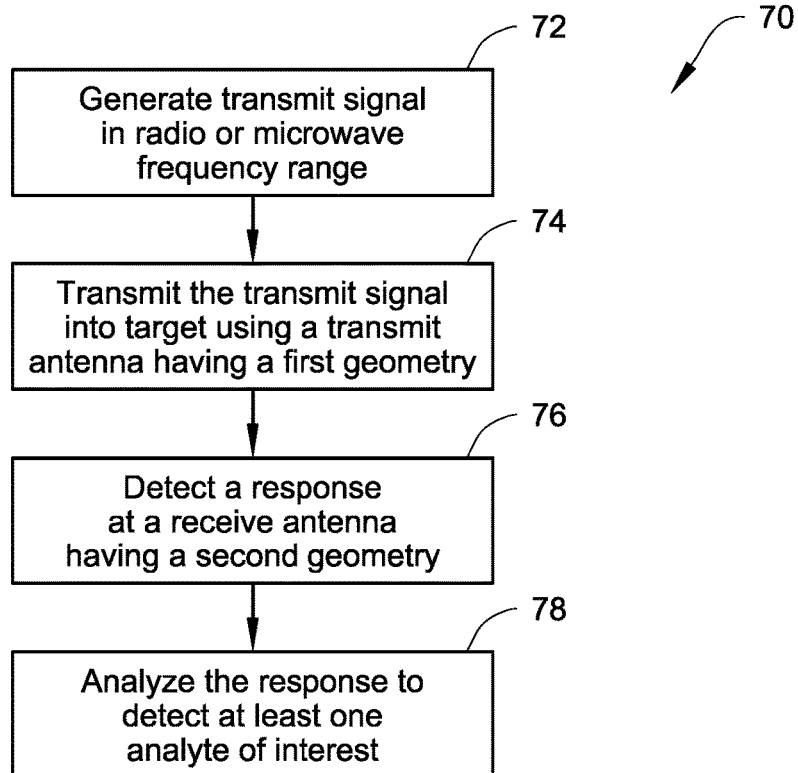
FIG. 6 is a flowchart of a method for detecting an analyte according to an embodiment.

With reference now to FIG. 6 together with FIG. 1, one embodiment of a method 70 for detecting at least one analyte in a target is depicted. The method in FIG. 6 can be practiced using any of the embodiments of the sensor device 5 described herein. In order to detect the analyte, the sensor device 5 is placed in relatively close proximity to the target. Relatively close proximity means that the sensor device 5 can be close to but not in direct physical contact with the target, or alternatively the sensor device 5 can be placed in direct, intimate physical contact with the target. The spacing between the sensor device 5 and the target 7 can be dependent upon a number of factors, such as the power of the transmitted signal. Assuming the sensor device 5 is properly positioned relative to the target 7, at box 72 the transmit signal is generated, for example by the transmit circuit 15. The transmit signal is then provided to the transmit antenna 11 which, at box 74, transmits the transmit signal toward and into the target. At box 76, a response resulting from the transmit signal contacting the analyte(s) is then detected by the receive antenna 13. The receive circuit 17 obtains the detected response from the receive antenna 13 and provides the detected response to the controller 19. At box 78, the detected response can then be analyzed to detect at least one analyte. The analysis can be performed by the controller 19 and/or by the external device 25 and/or by the remote server 27.

Figure 7:
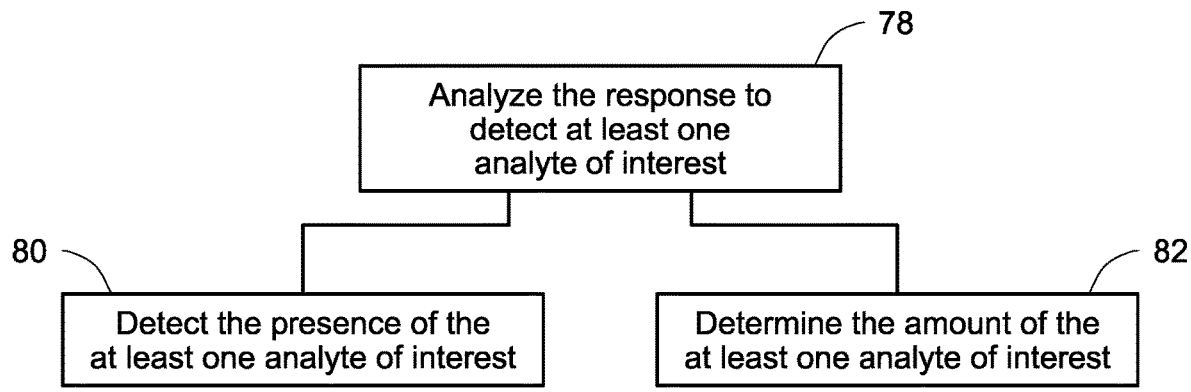
FIG. 7 is a flowchart of analysis of a response according to an embodiment.

Referring to FIG. 7, the analysis at box 78 in the method 70 can take a number of forms. In one embodiment, at box 80, the analysis can simply detect the presence of the analyte, i.e. is the analyte present in the target. Alternatively, at box 82, the analysis can determine the amount of the analyte that is present.

The interaction between the transmitted signal and the analyte may, in some cases, increase the intensity of the signal(s) that is detected by the receive antenna, and may, in other cases, decrease the intensity of the signal(s) that is detected by the receive antenna. For example, in one non-limiting embodiment, when analyzing the detected response, compounds in the target, including the analyte of interest that is being detected, can absorb some of the transmit signal, with the absorption varying based on the frequency of the transmit signal. The response signal detected by the receive antenna may include drops in intensity at frequencies where compounds in the target, such as the analyte, absorb the transmit signal. The frequencies of absorption are particular to different analytes. The response signal(s) detected by the receive antenna can be analyzed at frequencies that are associated with the analyte of interest to detect the analyte based on drops in the signal intensity corresponding to absorption by the analyte based on whether such drops in signal intensity are observed at frequencies that correspond to the absorption by the analyte of interest. A similar technique can be employed with respect to increases in the intensity of the signal(s) caused by the analyte.

Detection of the presence of the analyte can be achieved, for example, by identifying a change in the signal intensity detected by the receive antenna at a known frequency associated with the analyte. The change may be a decrease in the signal intensity or an increase in the signal intensity depending upon how the transmit signal interacts with the analyte. The known frequency associated with the analyte can be established, for example, through testing of solutions known to contain the analyte. Determination of the amount of the analyte can be achieved, for example, by identifying a magnitude of the change in the signal at the known frequency, for example using a function where the input variable is the magnitude of the change in signal and the output variable is an amount of the analyte. The determination of the amount of the analyte can further be used to determine a concentration, for example based on a known mass or volume of the target. In an embodiment, presence of the analyte and determination of the amount of analyte may both be determined, for example by first identifying the change in the detected signal to detect the presence of the analyte, and then processing the detected signal(s) to identify the magnitude of the change to determine the amount.

Notifications Regarding Detected Analytes

Figure 8:
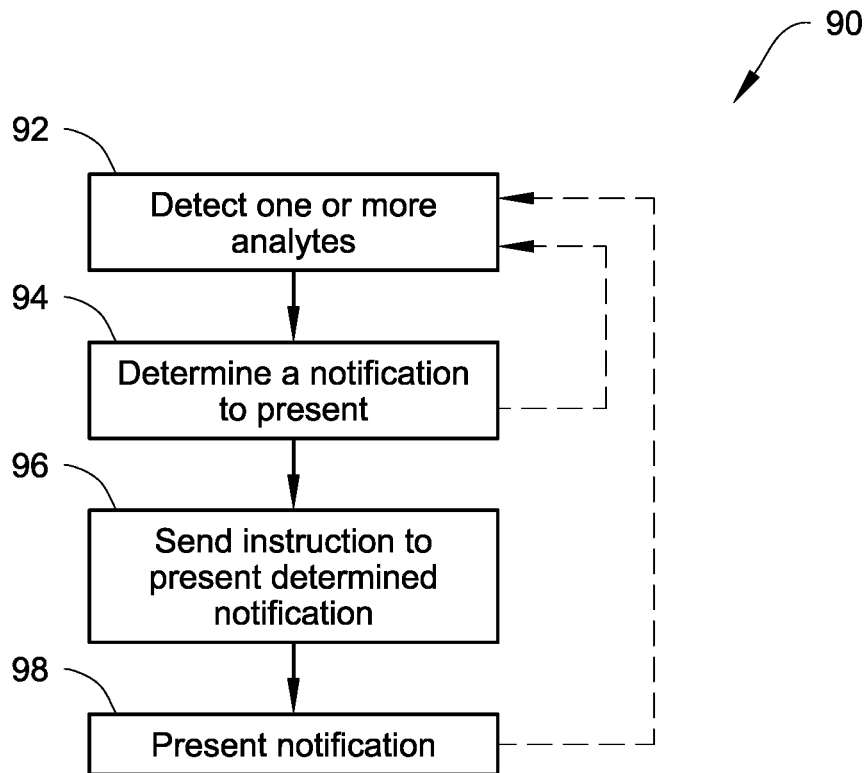
FIG. 8 is a flowchart of a method of providing a notification regarding one or more analytes according to an embodiment.

FIG. 8 is a flowchart of a method of providing a notification regarding one or more analytes according to an embodiment. The method 90 can include detecting one or more analytes 92, determining a notification to present 94, sending an instruction to present the determined notification 96, and providing the notification 98. The method 90 can be performed continuously, repeated iteratively, performed according to a predetermined schedule or sampling frequency, or when triggered by an event or a user prompt.

One or more analytes are detected at 92. The one or more analytes can include any of the analytes described herein. The detection of the one or more analytes at 92 can be performed using any of the sensors described herein. The detection of the one or more analytes can include detection of a presence and/or an amount of each of the one or more analytes. Each of the one or more analytes can be detected according to any of the methods described herein.

Determination of a notification to present occurs at 94. The determination of the notification to present at 94 is based on the one or more analytes detected at 92 and notification criteria. Satisfaction of notification criteria by the presence or amount of one or more of the analytes detected at 92 can be used determine the notification to present. In an embodiment, when no notification criteria are satisfied by the presence or amount of the one or more analytes, no notification to present may be determined. In an embodiment, method 90 can return from 94 to detection of the one or more analytes at 92 when no notification is determined to be presented at 94, for example when no notification criteria are satisfied by the presence or amount of analytes detected at 92. The determination is made at 94 using a processor that is configured to receive the results of the detection of the one or more analytes at 92. The notification criteria can be stored in a memory that is operatively connected to the processor that determines the presentation of the notification at 94, such that the processor can receive the notification criteria. The determination can be made at one or more devices, such as, for example, sensor 5, external device 25, or remote server 27 shown in FIG. 1 and described above.

In an embodiment, the notification criteria are such that the notification is determined at 94 based on the presence or amount of one analyte. In an embodiment, the notification criteria include an upper threshold, and it is determined that the notification is to be presented when the amount of the one analyte exceeds said upper threshold. In an embodiment, the presence of an analyte is represented as an upper threshold of 0, such that any amount of the analyte satisfies the notification criteria. In an embodiment, the notification criteria include a lower threshold, and the notification to present is determined when the amount of the analyte is below the lower threshold. In an embodiment, the analyte is glucose and the notification criteria include a lower threshold below which a notification indicative of low blood sugar is the notification to be presented. In an embodiment, the notification criteria include a bounded range for the analyte including both a lower threshold and also an upper threshold, and the criteria can be satisfied and the notification to present determined either when the amount of the analyte is within the bounded range or outside of the bounded range.

In an embodiment, the notification criteria used to determine the notification to present at 94 includes the presence or amount of each of a plurality of analytes. The notification criteria can include the states of each of the plurality of analytes, with said states of each of the analytes combined using any logical or conditional operators such as, as non-limiting examples, OR, AND, or IF-THEN statements. The states of each of the plurality of analytes can be whether that analyte satisfies an upper threshold, satisfies a lower threshold, is outside of a bounded range, or is within a bounded range as described above. A non-limiting example of notification criteria including a plurality of analytes is one satisfied when a first analyte is below a lower threshold and a second analyte is outside a bounded range. Another non-limiting example of a notification criteria including a plurality of analytes is one satisfied when either a first analyte is below a lower threshold, or a second analyte is below a lower threshold. The conditional or logical connectors can also be applied to combinations of states of analytes. A non-limiting example of such notification criteria is one satisfied if a third analyte is present when both a first analyte is above an upper threshold, and a second analyte is outside of a bounded range.

Once a notification to present is determined at 94, an instruction to present the determined notification is sent 96. In an embodiment, the instruction to present the determined notification sent at 96 is sent within a device from, for example, a processor of a device to one or more of a light, a display, a speaker, or a vibrating component included in the same device. In an embodiment, the instruction to present the determined notification sent at 96 is sent from one device to another, for example from sensor 5 to external device 25 shown in FIG. 1, from external device 25 to sensor 5, or from remote server 27 to one or both of the sensor 5 and external device 25. The instruction can be sent using, for example, wireless communications such as cellular data, Wi-Fi, Bluetooth, ZigBee, or any other suitable communications protocol for sending a message between devices. In an embodiment, the instruction can be a direct command to the one or more of a light, a display, a speaker, or a vibrating component. In an embodiment, the instruction can be a message within the context of a software application such as an app for a mobile device, the software application then presenting the determined notification using the one or more of a light, a display, a speaker, or a vibrating component.

The notification can be provided at 98. The notification can include one or more of a visual component, an audible component or a tactile component. The notification can be provided at a device such as, for example sensor 5 or external device 25 shown in FIG. 1 and described above. The notification can be provided at 98 to a subject in whom the analyte is measured, such as a wearer or sensor 5 or where external device 25 is a smart phone, tablet, computer, or other device of the subject. The notification can be provided at 98 to a recipient other than a subject in whom the analyte is being measured, for example, medical or other care personnel, or when the analyte being sensed at 92 is not within a human subject, for example where the external device 25 is a smart phone, table, computer, or other device of a person in which the analyte is not being detected.

The visual component can include, as non-limiting examples, display of a light, presenting a color of a light, control of a frequency or pattern of flashing of a light, presenting a still or animated image using a display or projector, or presenting text using a display or projector. The text may be indicative, for example, of a condition associated with the presence or amount of the one or more analytes detected at 92, for example providing text indicating low blood sugar when the analyte is glucose and it is below a lower threshold included in the notification criteria. In an embodiment, text included as a visual component may direct corrective action, such as suggesting eating when the analyte is glucose and it is below a lower threshold included in the notification criteria. The visual component can be presented at 98 using one or more lights such as LED lights or a display included on a device such as, for example, sensor 5 or external device 25 shown in FIG. 1 and described above.

The audible component can include, as non-limiting examples, one or more tones, a pattern of producing the one or more tones, a repeating alarm, playing of a voice message including speech, or any other suitable audible notification. The voice message may be indicative, for example, of a condition associated with the presence or amount of the one or more analytes detected at 92, for example providing text indicating low blood sugar when the analyte is glucose and it is below a lower threshold included in the notification criteria. In an embodiment, voice message included as an audible component may direct corrective action, such as suggesting eating when the analyte is glucose and it is below a lower threshold included in the notification criteria. The audible component can be presented at 98 using, for example, a speaker included on a device such as, for example, sensor 5 or external device 25 shown in FIG. 1 and described above.

The tactile component can include, as non-limiting examples, vibration of a device, the pattern or frequency of vibration of the device, or the like. The tactile component can include haptic feedback. The tactile component can be presented at 98 using a vibrating component included on a device such as, for example, sensor 5 or external device 25 shown in FIG. 1 and described above.

Any of the visual, audible, and tactile components can be combined to form the notification presented at 98. The notification can be indicative of the presence or amount of the one or more analytes associated with the notification criteria used to direct presentation of that notification.

As indicated above, the data obtained by the sensor 5 needs to be analyzed, for example by determining a notification to present based on said data as described above. The analysis can occur on the sensor 5 or on one or more devices or systems separate from the sensor 5. Unless otherwise indicated by the Applicant, the term devices or systems is intended to be construed broadly as encompassing any type of devices or systems that can analyze the data obtained by the sensor 5. Examples of devices or system that can be used to analyze the data include, but are not limited to, hardware-based computing devices or systems; cloud-based computing devices or systems; machine learning devices or systems including active learning devices or systems; artificial intelligence-based devices or systems; neural network-based devices or systems; combinations thereof; and any other types of devices and systems that are suitable for analyzing the data.

One or more output signals resulting from or based on the analysis are then generated. In some embodiments, the output signal(s) is generated by the device(s) or system(s) that analyze the data. The output signal(s) is directed to one or more other devices or systems that implement an action based on the output signal(s). In one embodiment, the output signal(s) is directed to one or more notification devices (discussed further below) which generates at least one human perceptible notification for example to provide a perceptible signal or alert to the patient and/or a caregiver of the patient. In this embodiment, the output signal(s) may be referred to as a notification signal(s). In another embodiment, the output signal(s) may be directed to one or more other machine(s) or system(s), for example a medical device such as an insulin pump, that modifies the operation of the other machine(s) or system(s). In one embodiment, the output signal(s) or separate output signals can be directed to both one or more notification devices and one or more other machine(s) or system(s). In one embodiment, the output signal(s) can be stored in a suitable data storage separately from, or in addition to, being sent to one or more notification devices and/or to one or more other devices or systems.

Figure 9:
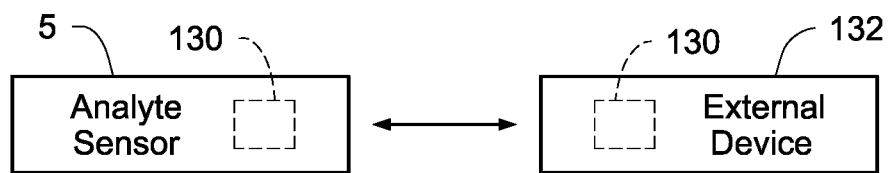
FIG. 9 depicts a system that includes the analyte sensor and an external device in communication with the analyte sensor, with the system including a notification device.

FIG. 9 illustrates one non-limiting example of an output signal generation. In this example, an output signal is sent to a notification device 130 included in the system 100 to generate at least one human perceptible notification resulting from the analysis. The notification device 130 can be connected, directly or indirectly, to the system 100. For example, in one embodiment, the notification device 130 can be incorporated on the sensor 5 to provide the at least one human perceptible notification directly to the person using or wearing the sensor 5. In another embodiment, the notification device 130 can be incorporated into a device 132 that is physically separate from the sensor 5 including, but not limited to, a mobile phone (a.k.a. cell phone, smartphone); a tablet computer; a laptop computer; a personal computer; a wearable device such as a watch or a head-mounted device or clothing; a video game console; furniture such as a chair; a vehicle such as a car, automobile or truck; lightbulbs; smart home appliances such as a smart refrigerator; and a use specific device similar to these devices that is specifically designed to function with the sensor 5. The at least one human perceptible notification generated by the notification device 130 can be one or more of an audible sound notification, a visual notification, a haptic notification, or an olfactory notification. Operation of the notification device 130 can be triggered by a notification or output signal that is generated resulting from the analysis. The notification signal can be generated by the sensor 5, for example by the main controller thereof, or by a separate device or system as described above that performs the analysis after receiving the data from the sensor 5.

The terminology used in this specification is intended to describe particular embodiments and is not intended to be limiting. The terms "a," "an," and "the" include the plural forms as well, unless clearly indicated otherwise. The terms "comprises" and/or "comprising," when used in this specification, specify the presence of the stated features, integers, steps, operations, elements, and/or components, but do not preclude the presence or addition of one or more other features, integers, steps, operations, elements, and/or components.

The examples disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:

1. A method for providing notification regarding one or more analytes, comprising:
non-invasively detecting the one or more analytes, wherein non-invasively detecting the one or more analytes comprises:
generating a transmit signal having a frequency that falls within a range of between about 10 kHz to about 100 GHz;
transmitting the transmit signal into a target containing at least one analyte of interest from at least one transmit element, the at least one transmit element has parallel side edges, a first end, and a second end, the first and second ends have a first geometry; and
using at least one receive element to detect a response resulting from transmitting the transmit signal by the at least one transmit element into the target containing the at least one analyte of interest, the at least one receive element has parallel side edges, a first end, and a second end, and the first end and the second end of the at least one receive element have a second geometry that differs from the first geometry;
determining a presence or an amount of each of the one or more analytes based on the response;
determining a notification to present based on the presence or amount of at least one of the one or more analytes and notification criteria using a processor; and
sending an instruction directing presentation of the notification.

2. The method of claim 1, further comprising presenting the notification.

3. The method of claim 2, wherein presenting the notification includes one or more of a visual component, an aural component, or a tactile component.

4. The method of claim 2, wherein the notification is presented at the non-invasive sensor.

5. The method of claim 2, wherein the notification is presented at an external device, separate from the non-invasive sensor.

6. The method of claim 1, wherein the notification criteria include a lower threshold value, and the notification to be presented is determined based on whether the amount of one analyte is below the lower threshold value.

7. The method of claim 6, wherein the analyte is glucose and the notification is indicative of a low blood sugar condition.

8. The method of claim 1, wherein the notification criteria include an upper threshold value, and the notification to be presented is determined based on whether the amount of one of the one or more analytes is above the upper threshold value.

9. The method of claim 1, wherein the notification criteria include a lower threshold value and an upper threshold value, and the notification to be presented is determined based on whether the amount of one of the one or more analytes is below the lower threshold value or above the upper threshold value.

10. The method of claim 1, wherein the at least one transmit element and the at least one receive element are disposed side-by-side with each other;
the at least one transmit element has a first length, the at least one receive element has a second length, and the first length equals the second length;
the at least one transmit element has a first width, the at least one receive element has a second width, and the first width equals the second width.

11. A method for providing notification regarding one or more analytes, comprising:
non-invasively detecting the one or more analytes, wherein non-invasively detecting the one or more analytes comprises:

generating a transmit signal having a frequency that falls within a range of between about 10 kHz to about 100 GHz;

transmitting the transmit signal from at least one transmit element into a target containing at least one analyte of interest, the at least one transmit element has parallel side edges, a longitudinal axis, a first end, and a second end, the first and second ends have a first geometry; and detecting a response resulting from transmitting the transmit signal by the at least one transmit element into the target containing the at least one analyte of interest using at least one receive element, the at least one receive element has parallel side edges, a longitudinal axis, a first end, and a second end, and the first end and the second end of the at least one receive element have a second geometry that differs from the first geometry, and the longitudinal axis of the at least one transmit element is parallel to the longitudinal axis of the at least one receive element;

determining a presence or an amount of each of the one or more analytes based on the response;

determining a notification to present based on the presence or amount of at least one of the one or more analytes and notification criteria using a processor; and sending an instruction directing presentation of the notification.

12. The method of claim 11, further comprising presenting the notification.

13. The method of claim 12, wherein presenting the notification includes one or more of a visual component, an aural component, or a tactile component.

14. The method of claim 12, wherein the notification is presented at the non-invasive sensor.

15. The method of claim 12, wherein the notification is presented at an external device, separate from the non-invasive sensor.

16. The method of claim 11, wherein the notification criteria include a lower threshold value, and the notification to be presented is determined based on whether the amount of one analyte is below the lower threshold value.

17. The method of claim 16, wherein the analyte is glucose and the notification is indicative of a low blood sugar condition.

18. The method of claim 11, wherein the notification criteria include an upper threshold value, and the notification to be presented is determined based on whether the amount of one of the one or more analytes is above the upper threshold value.

19. The method of claim 11, wherein the notification criteria include a lower threshold value and an upper threshold value, and the notification to be presented is determined based on whether the amount of one of the one or more analytes is below the lower threshold value or above the upper threshold value.

20. The method of claim 11, wherein the at least one transmit element and the at least one receive element are disposed side-by-side with each other;

the at least one transmit element has a first length, the at least one receive element has a second length, and the first length equals the second length;

the at least one transmit element has a first width, the at least one receive element has a second width, and the first width equals the second width.

* * * * *